(12) United States Patent
Bussell

(10) Patent No.: US 11,992,448 B2
(45) Date of Patent: May 28, 2024

(54) COMPUTER-SUPPORTED INTRANEURAL FACILITATION FOR VASCULAR CHANGES

(71) Applicant: LOMA LINDA UNIVERSITY, Loma Linda, CA (US)

(72) Inventor: Mark Bussell, Loma Linda, CA (US)

(73) Assignee: LOMA LINDA UNIVERSITY, Loma Linda, CA (US)

( * ) Notice: Subject to any disclaimer, the term of this patent is extended or adjusted under 35 U.S.C. 154(b) by 804 days.

(21) Appl. No.: 15/733,752

(22) PCT Filed: Apr. 23, 2019

(86) PCT No.: PCT/US2019/028593
§ 371 (c)(1),
(2) Date: Oct. 16, 2020

(87) PCT Pub. No.: WO2019/209754
PCT Pub. Date: Oct. 31, 2019

(65) Prior Publication Data
US 2021/0137763 A1 May 13, 2021

Related U.S. Application Data

(60) Provisional application No. 62/661,568, filed on Apr. 23, 2018.

(51) Int. Cl.
*A61B 8/00* (2006.01)
*A61B 8/06* (2006.01)
(Continued)

(52) U.S. Cl.
CPC ............. *A61H 1/0222* (2013.01); *A61B 8/06* (2013.01); *A61B 8/463* (2013.01); *A61B 8/488* (2013.01);
(Continued)

(58) Field of Classification Search
CPC ..... A61B 8/488; A61H 1/0218; A61H 1/0266
See application file for complete search history.

(56) References Cited

U.S. PATENT DOCUMENTS

| 6,023,968 A | 2/2000 | Spratt et al. |
| 2005/0137479 A1 | 6/2005 | Haider |

(Continued)

OTHER PUBLICATIONS

International Search Report and Written Opinion for PCT/US2019/028593, dated Aug. 1, 2019.
(Continued)

*Primary Examiner* — Rajeev P Siripurapu
(74) *Attorney, Agent, or Firm* — Womble Bond Dickinson (US) LLP

(57) ABSTRACT

The disclosure is related to a system and method for operating a traction device to detect blood flow patterns in a subject for managing neuropathy related conditions through intraneural facilitation (INF). According to an embodiment, the INF system and method rely on the traction device for positioning the subject in one or more positions, and a processing device for processing intervening signals obtained by a probe positioned on the subject. The signals received from the probe may be used to determine a two dimensional (2D) plane blood flow pattern. Detected changes in the measured blood flow may be used to determine if further traction device positions are required to ensure that the intervening signals demonstrate normal blood flow patterns with improvements to the neuropathy condition. The 2D flow pattern may calculate at least one of Volume Flow (VF) and Pulsatility Index (PI) for each set of signals received.

20 Claims, 9 Drawing Sheets

(51) Int. Cl.
*A61B 8/08* (2006.01)
*A61H 1/02* (2006.01)
(52) U.S. Cl.
CPC ......... *A61H 1/0266* (2013.01); *A61H 1/0285* (2013.01); *A61H 1/0288* (2013.01); *A61H 2201/1207* (2013.01); *A61H 2201/5007* (2013.01); *A61H 2201/5058* (2013.01); *A61H 2203/0456* (2013.01); *A61H 2230/255* (2013.01)

(56) References Cited

U.S. PATENT DOCUMENTS

| | | |
|---|---|---|
| 2009/0005675 A1 | 1/2009 | Grunwald et al. |
| 2012/0150077 A1 | 6/2012 | Bussell |
| 2016/0228019 A1 | 8/2016 | Grunwald et al. |
| 2017/0296209 A1* | 10/2017 | Morganstern ...... A61K 41/0028 |
| 2019/0159728 A1* | 5/2019 | Pritchard ............. A61B 8/4209 |

OTHER PUBLICATIONS

Van Der Wey LP et al: "A model for monitoring nerve blood flow during expansion by laser Doppler flowmetry in the rabbit", Journal of Neurological Sciences, Elsevier Scientific Publishing Co, Amsterdam, NL, vol. 117, No. 1-2, Jul. 1, 1993 (Jul. 1, 1993), pp. 79-82.

* cited by examiner

COMPUTER-SUPPORTED INTRANEURAL FACILITATION FOR VASCULAR CHANGES

CROSS-REFERENCE TO RELATED APPLICATIONS

This application is a PCT application and claims priority to, and the benefit of, U.S. Provisional Application No. 62/661,568, filed Apr. 23, 2018, titled "COMPUTER-SUPPORTED INTRANEURAL FACILITATION FOR VASCULAR CHANGES," which is incorporated herein by reference in its entirety.

BACKGROUND

1. Field of Invention

The present technology relates generally to intraneural facilitation and, more particularly, to a method and system directed to operating a traction device to detect blood flow patterns for intraneural facilitation.

2. Description of the Prior Art

Neurovascular insufficiency refers to decreased blood supply to the network of blood vessels, and has a variety of causes, such as body system failure or trauma. For example, neurovascular insufficiency (also referred to as neuropathy) may come from local capillary closure within the nerve, decreased blood flow within a local artery, poor control of the artery by the sympathetic nerves, mechanical trauma or vascular insufficiency of a nerve root, or metabolic ischemia associated with the paravertebral ganglia. Intraneural Facilitation (INF) treatment is commonly used to restore blood flow to the damaged nerves and eliminate the pain, tingling, and numbness and other symptoms that often accompany neuropathy.

INF treatment is administered in order to bring more blood into the local nerve where the symptoms are identified, or to address the nerve with the most inflammation or that is the most symptomatic. For example, the strangulation of the blood at a foot in a human subject may be caused by a distant problem such as ischemia at the paravertebral ganglion, which may impact the nerve blood flow to the sympathetic nerve that regulates the circulation at the foot. However, even if the local nerve at the foot near the symptoms is treated, the improved circulation in the plantar nerves may not reach the ischemic paravertebral ganglion where the distant problem originated. Thus, the real problem that causes neuropathy is not resolved with INF and the symptoms will reoccur.

There is lacking an accurate system that can assist INF in providing the necessary calculations and data to guide where the treatment can be best administered. Peripheral neuropathy is most commonly diagnosed using Electromyography (EMG) and a Nerve Conduction Study (NCS). The EMG, however, does not provide real-time information regarding distant verses local neurovascular control, and the relationship between the large arteries and nerves, and is not useful for INF administration. EMG analysis may show that there is vascular ischemia creating neuropathy, however it is not practical or possible for the needed vascular calculations to be generated by the EMG. The EMG monitors electrical signals and is useful for diagnosing muscle disorders, nerve disorders, and disorders affecting the connection between nerves and muscles. The EMG will not show the impact these disorders have on the neurovascular system quantitatively, however, which is needed to guide a neurovascular treatment such as INF.

Further, neuropathic inflammation and reported numbness or pain in the foot may illustrate that local administration of INF may not address the real problem. The first vascular track involving the dura mater (the tough outermost membrane enveloping the brain and spinal cord) and connection at the nerve root may impact the venous return, creating venous stasis and preventing endoneurial capillary circulation from flowing freely in the cutaneous capillary bed of the foot. Proximal paravertebral ganglion ischemia in the torso means that ischmia will impact and create hypofunction or hyperfunction of sympathetic nerves traveling into the skin of the neuropathic foot. A doral ganglion nerve root impingement may impact the endoneurial circulation of sensory nerve flowing into the capillaries of the skin of the foot that has neuropathic inflammation. Or, it may be the local capillaries of the skin of the foot that are impacted, along with other systems that are impacted by the circulation to the foot.

Often in neuropathy the nerve trunks are impacted, and the patient may notice only the worst symptoms, but may not be able to identify all the systems and nerves that are compromised. Clinical sensory testing may show the performance of afferents or efferents, but is often inconclusive with respect to showing vascular discrepancies or indicating which systems are impacting the vascular systems.

Neuropathy is presently not capable of being effectively and holistically addressed by physical therapy methods or by devices. Neuropathic pain and nerve debilitation resulting in paralysis are not presently treated with consistency. Moreover, peripheral neuropathy remains elusive and incurable.

SUMMARY

Applicant has recognized the difficulties noted above and that there is an unmet need for a system and method for administering INF treatment with precision and accuracy to treat neuropathy. Applicant has recognized that the state of the art is lacking an objective way to measure circulation with respect to a nerve, and measure numerically whether there is normal circulation. There is further lacking an objective method to control blood flow distally and proximally in a manner that consistently and precisely impacts nerve circulation. Through detailed testing and analysis, Applicant has recognized that, if the distal control of the nerve blood flow is failing, a circulation calculation may be used to demonstrate this failing, and INF may be administered to the problematic nerves distant from the location of the symptoms. These calculations may also be used to show if the immune systems are impacting local vascular control of large vessels, and if local nerves are receiving the circulation appropriately.

The present disclosure is directed to an embodiment of a method of operating a traction device to detect blood flow patterns for intraneural facilitation (INF) treatment, the method including providing the traction device to control traction, by one or more processors, so as to position a subject in one or more positions when positioned on one or more areas of the subject. The method can further include receiving first signals, by the one or more processors, from a probe when the probe is positioned at a first area of the subject and when the traction device is positioned in a first position. In an embodiment, the method can further include processing the received first signals, via the one or more processors, to determine a first two-dimensional (2D) flow pattern measuring blood flow when being supplied from a first artery to a second artery supplying the blood flow to one or more nerves of the subject. According to an embodiment, the method can further include moving the traction device to a second position, via the one or more processors, based at least in part on the determined first 2D flow pattern, thereby to control the blood flow for a first predetermined period of time. The method can further include receiving second signals, by the one or more processors, from the probe when the probe is positioned at one or more second areas of the subject and when the traction device is positioned in the second position. The method can further include processing the received second signals, via the one or more processors, to determine a second 2D flow pattern measuring the blood flow from the first artery to the second artery. In an embodiment, the method can further include comparing the first 2D flow pattern and the second 2D flow pattern, via the one or more processors, to determine a first change in the blood flow through the second artery, thereby to provide vascular changes in the subject via INF.

According to an embodiment, the determined first change in the blood flow may include a decrease in the blood flow through the second artery, such that the method can further include moving the traction device to a third position, via the one or more processors, based at least in part on the comparing, thereby to control the blood flow for a second predetermined period of time. The method can further include receiving third signals, by the one or more processors, from the probe when the probe is positioned at the one or more second areas of the subject and when the traction device is positioned in the third position. The method can further include processing the received third signals, via the one or more processors, to determine a third 2D flow pattern measuring the blood flow from the first artery to the second artery. The method can further include comparing the second 2D flow pattern and the third 2D flow pattern, via the one or more processors, to determine a second change in the blood flow through the second artery.

In an embodiment, the determined second change in the blood flow can include an increase in the blood flow through the second artery, such that the method can further include moving the traction device to a fourth position, via the one or more processors, based at least in part on the comparing, thereby to alter the blood flow. The method can further include receiving fourth signals, by the one or more processors, from the probe when the probe is positioned at the one or more second areas of the subject and when the traction device is positioned in the fourth position. The method can further include processing the received fourth signals, via the one or more processors, to determine a fourth 2D flow pattern measuring the blood flow from the first artery to the second artery. The method can further include comparing the first 2D flow pattern and the fourth 2D flow pattern, via the one or more processors, to confirm the increase in blood flow through the second artery.

The present disclosure is also directed to a system for operating a traction device to detect blood flow patterns for intraneural facilitation (INF), the system including one or more processors; one or more traction devices to control traction, by the one or more processors, so as to position a subject in one or more positions when positioned on one or more areas of the subject; one or more probes connected to the one or more processors to supply signals when applied to one or more areas of the subject; and one or more memory devices in communication with the one or more processors, according to an embodiment. In an embodiment, the one or more memory devices can include instructions that, when executed in the one or more processors, cause the system to receive first signals from the probe when the probe is positioned at the first area of the subject and when the traction device is positioned in a first position; process the received first signals to provide a first display of a first two-dimensional (2D) flow pattern measuring blood flow when being supplied from a first artery to a second artery supplying the blood flow to one or more nerves of the subject; move the traction device to a second position based at least in part on the determined first 2D flow pattern, thereby to control the blood flow for a first predetermined period of time; receive second signals from the probe when the probe is positioned at one or more second areas of the subject and when the traction device is positioned in the second position thereby to control the blood flow for a first predetermined period of time; process the received second signals to provide a second display of a second 2D flow pattern measuring the blood flow from the first artery to the second artery; and compare the first 2D flow pattern and the second 2D flow pattern to determine a first change in the blood flow through the second artery, thereby to provide vascular changes in the subject via INF.

In an embodiment, the determined first change in the blood flow can include a decrease in the blood flow through the second artery. According to an embodiment, the instructions can further cause the system to move the traction device to a third position based at least in part on the comparing, thereby to control the blood flow for a second predetermined period of time; receive third signals from the probe when the probe is positioned at the one or more second areas of the subject and when the traction device is positioned in a third position; process the received third signals to provide a third display of a third 2D flow pattern measuring the blood flow from the first artery to the second artery; and compare the second 2D flow pattern and the third 2D flow pattern to determine a second change in the blood flow through the second artery.

According to an embodiment, the determined second change in the blood flow can include an increase in the blood flow through the second artery. In an embodiment, the instructions can be further configured to cause the system to move the traction device to a fourth position based at least in part on the comparing, thereby to alter the blood flow; receive fourth signals from the probe when the probe is positioned at the one or more second areas of the subject and when the traction device is positioned in the fourth position; process the received fourth signals to provide a fourth display of a fourth 2D flow pattern measuring the blood flow from the first artery to the second artery; and compare the first 2D flow pattern and the fourth 2D flow pattern to confirm the increase in blood flow through the second artery.

The data collected from the method for operating a traction device to detect blood flow patterns for INF may provide insight into INF treatment progress and nerve healing status. The method may be also able to guide INF as to whether the INF treatment has successfully brought circulation into the intended tissue. Furthermore, the method may be used to demonstrate the extent of the patient's vascular progress.

Other aspects and features of the present disclosure will become apparent to those of ordinary skill in the art after reading the detailed description herein and the accompanying figures.

BRIEF DESCRIPTION OF THE DRAWINGS

Some of the features and benefits of the present disclosure having been stated, others will become apparent as the description proceeds when taken in conjunction with the accompanying drawings, in which.

Figure 1A:
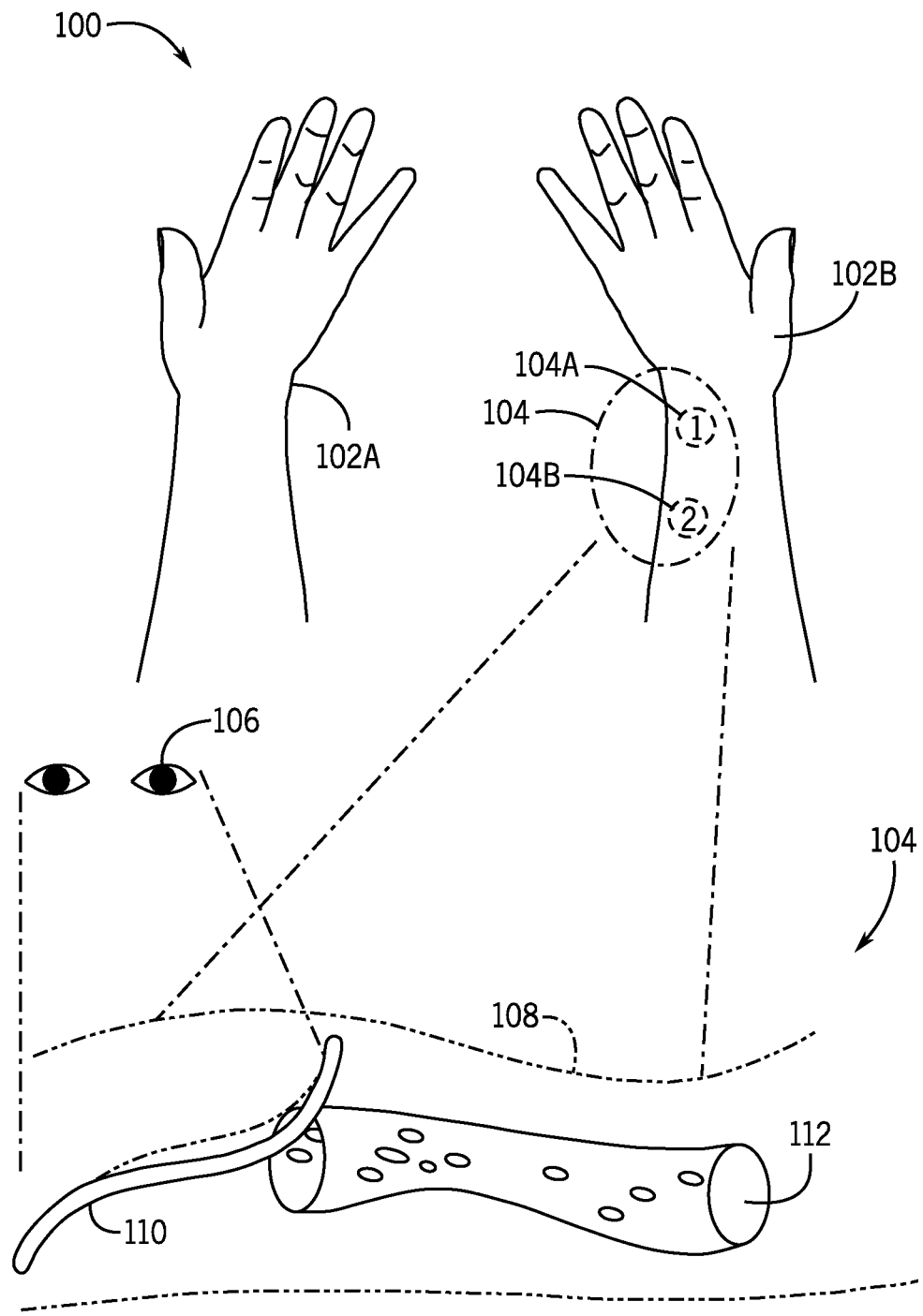
FIG. 1A illustrates a general overview of physical therapy by observing muscle in accordance with various embodiments.

While the disclosure will be described in connection with the preferred embodiments, it will be understood that it is not intended to limit the disclosure to that embodiment. On the contrary, it is intended to cover all alternatives, modifications, and equivalents, as may be included within the spirit and scope of the disclosure as defined by the appended claims.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Systems and methods in accordance with various embodiments of the present disclosure may overcome one or more of the aforementioned and other deficiencies experienced in conventional approaches to managing neuropathy arising from any condition in a human or other mammal subject. In an example, a computer-implemented method is disclosed for intraneural facilitation (INF) for vascular changes. According to an embodiment, the computer-implemented method can include receiving first signals from a probe at a first area of a human subject. The first signals can be processed to provide a first two-dimensional (2D) flow pattern associated with blood flow from a first artery to a second artery supplying at least one nerve of the human subject. Such a process can include identifying discriminant features from the first signals. The discriminant features can be velocity values clustering in a 2D plane. According to an embodiment, a first physical change can be caused in the first area of the human subject. For example, the physical change can include turning a foot joint of the human subject, via a traction device, to control the blood flow in the area of the foot joint for a first predetermined period of time. Second signals from the probe can be processed after causing the first physical change. As in the case of the first signals, the processing of the second signals can provide a second 2D flow pattern associated with the blood flow. The second 2D flow pattern can demonstrate a reduction in the blood flow through the second artery, according to an embodiment.

The second 2D flow pattern can be useful in determining how to cause second physical changes in one or more second areas of the human subject. For example, a distal area, such as a finger of the human subject, can be subjected to the second physical changes via the traction device, according to an embodiment. The second physical changes can be made so as to control the blood flow for a second predetermined period of time. Third signals from the probe can be processed after causing the second physical change. The processing of the third signals can provide a third 2D flow pattern associated with the blood flow. The third 2D flow pattern can demonstrate an increase in the blood flow through the second artery, according to an embodiment. The first physical change can be maintained, along with the second physical changes, via the traction device, for a third predetermined period of time. This can increase the blood flow through the second artery, as demonstrated from the third 2D flow pattern. Once completed, the first physical change and the second physical changes can be released, via the traction device, to provide a fourth 2D flow pattern that is different from the first 2D flow pattern and that confirms that the neuropathy is managed, according to an embodiment.

An embodiment of a system is also described that can include at least one traction system and memory including instructions for execution by at least one processor to provide the above-referenced processing steps. The above-referenced processing steps can be used by the system, along with physical changes to the human subject caused by the at least one traction system, to generate or provide discriminant features from each of the first, second, and third signals. The discriminant features in each case (e.g., of the first, the second, and third signals), can be velocity values clustering in a 2D plane to support a determination that a neuropathy issue is identified and is being managed.

Various other functions can be implemented within the various embodiments, as well as discussed and suggested elsewhere herein.

As used herein and unless indicated otherwise, sympathetic nerves generally refer to nerves that function to constrict blood vessel smooth muscle without intentional actions. The epineurium generally refers to an outer area, an outer layer, an outer chamber, or an outside fascicle of an arteriole, unless indicated otherwise. The endoneurium generally refers to an inner tissue of the fascicle where oxygen is exchanged between an associated nerve and associated capillaries, unless otherwise indicated. The perineurium generally refers to a tough dividing neural tissue layer that may exist between outer and inner chambers or fascicles, unless otherwise indicated. The transperineurial vessels, as used herein and unless indicated otherwise, generally refer to nerves that bring blood from an outer layer or chamber of the fascicle (e.g., the epineurium) to an inner layer of the fascicle (e.g., the endoneurium). The peripheral nervous system generally includes nerves in the legs and arms, while the central nervous system generally includes nerves in the spinal cord and head. Arterioles, as used herein and unless indicated otherwise, generally refer to small arteries with at least a smooth muscle that is innervated. Perivascular plexus, as used herein and unless indicated otherwise, generally refers to a cluster of nerves that surround an artery or arteriole and innervate the smooth muscle of the arteriole or artery.

Figure 4:
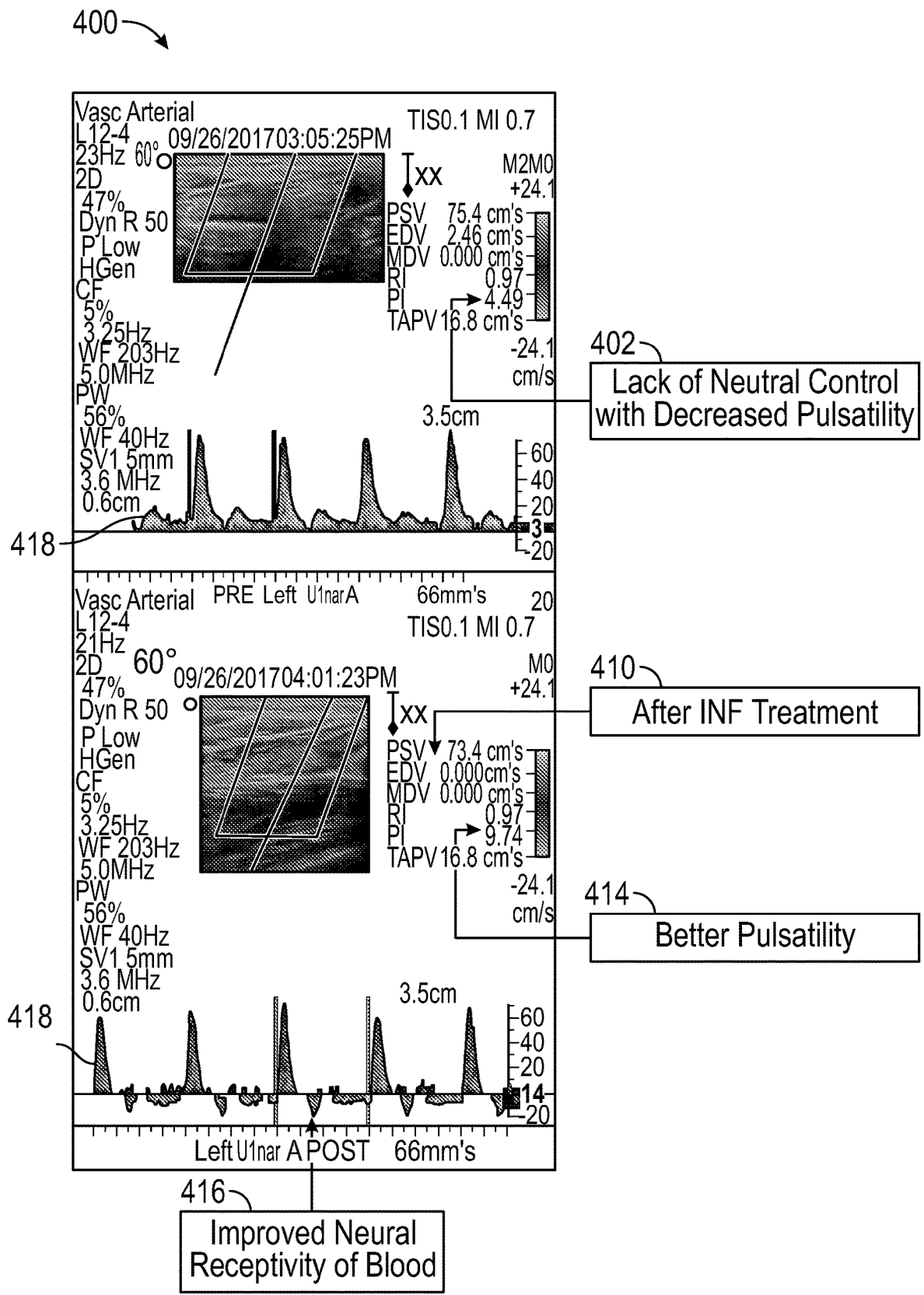
FIG. 4 illustrates an example of various blood flow patterns and related information in a computer-supported INF for vascular changes in accordance with aspects of this disclosure.
Figure 4:
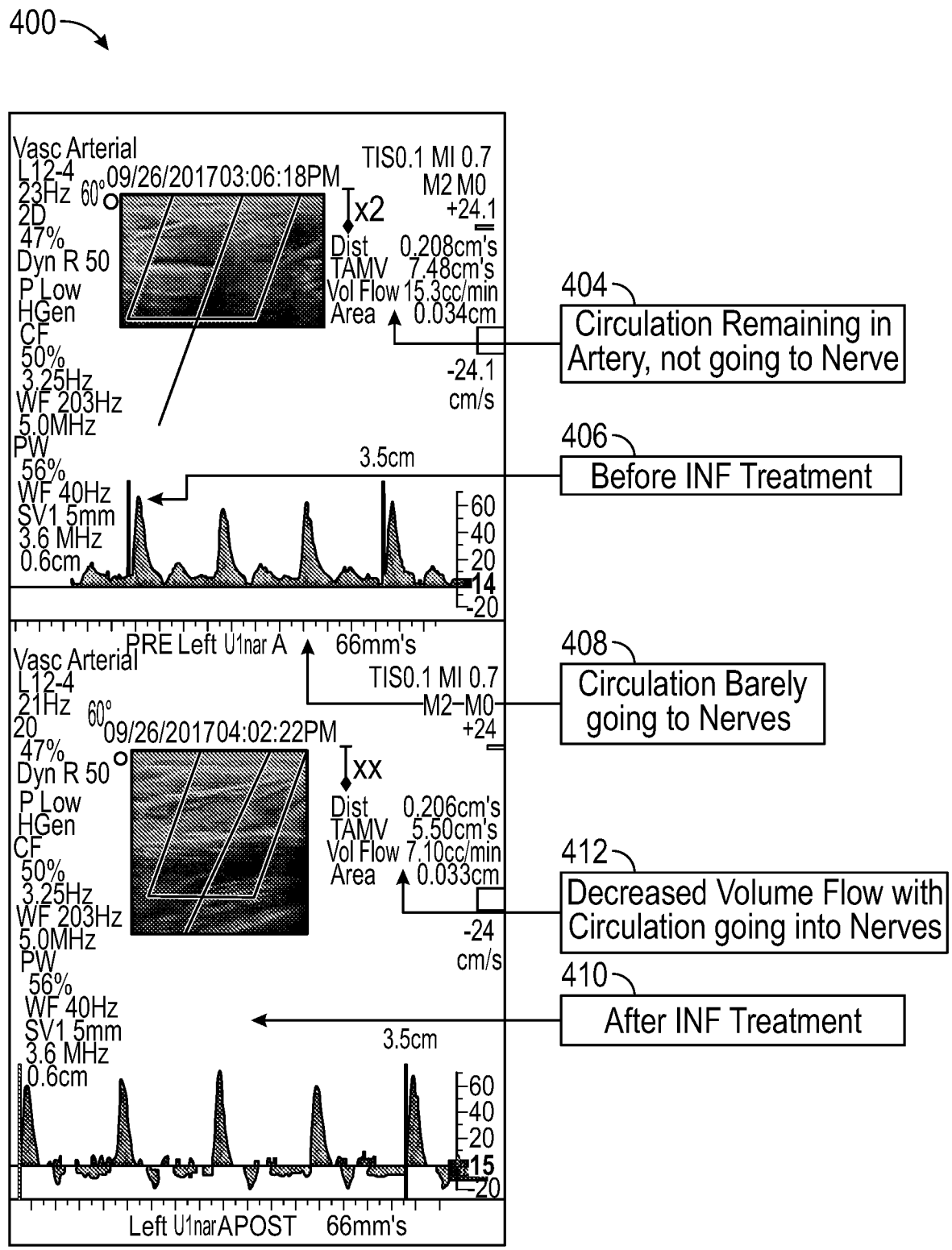

The present disclosure uses traction systems to provide traction control to at least two areas, which are selected to target extremities on a human or other mammal subject, with intervening signal processing (for example as illustrated in FIG. 4, and discussed in more detail below) to determine blood flow patterns that are then used to further control the traction systems. As a result, the systems and methods described herein address tissues, nerves, tracks, and arterial chambers that are in greatest need of neural revascularization. The present systems and methods allow accurate targeting of specific hydraulic or electrical needs of a nerve by use of the intervening signal processing steps and control offered by the targeted traction control. The present systems and methods identify and target the central nervous system (CNS) region that is ischemic and not responding to increased neural activity, and which is indirectly creating peripheral nerve vascular slowing.

FIG. 1A is a partial detailed view illustrating hands and wrists 102A, 102B of a human subject with neuropathy from an underlying condition. The illustrated embodiment demonstrates a known treatment method, in which the neuropathy may be treated in a subjective manner by application of physical pressure at pressure points 104A, 104B while visually monitoring 106 for tone changes in muscle 110 within surrounding tissue 108. Chemotherapy-induced peripheral neuropathy (CIPN) may be one such underlying condition, which is a progressive condition accompanied by pain, tingling, and sensitivity in the hands and feet. This condition may occur in patients undergoing chemotherapy. Other conditions that may have accompanying neuropathy include injuries, chronic pain syndromes, and other medical conditions, as will be readily understood by one of ordinary skill in the art. Pressure points 104 may be chosen for their proximity to the area under neuropathy. While the intent is to drive blood through artery 112 by applying pressure to the pressure points 104, this process has no specific indications of success and may represent an inaccurate and testing-based process. References to parts of the human subject, e.g., hands 102A, 102B, are used interchangeably with a reference to a human subject as a whole, unless indicated otherwise.

Figure 1B:
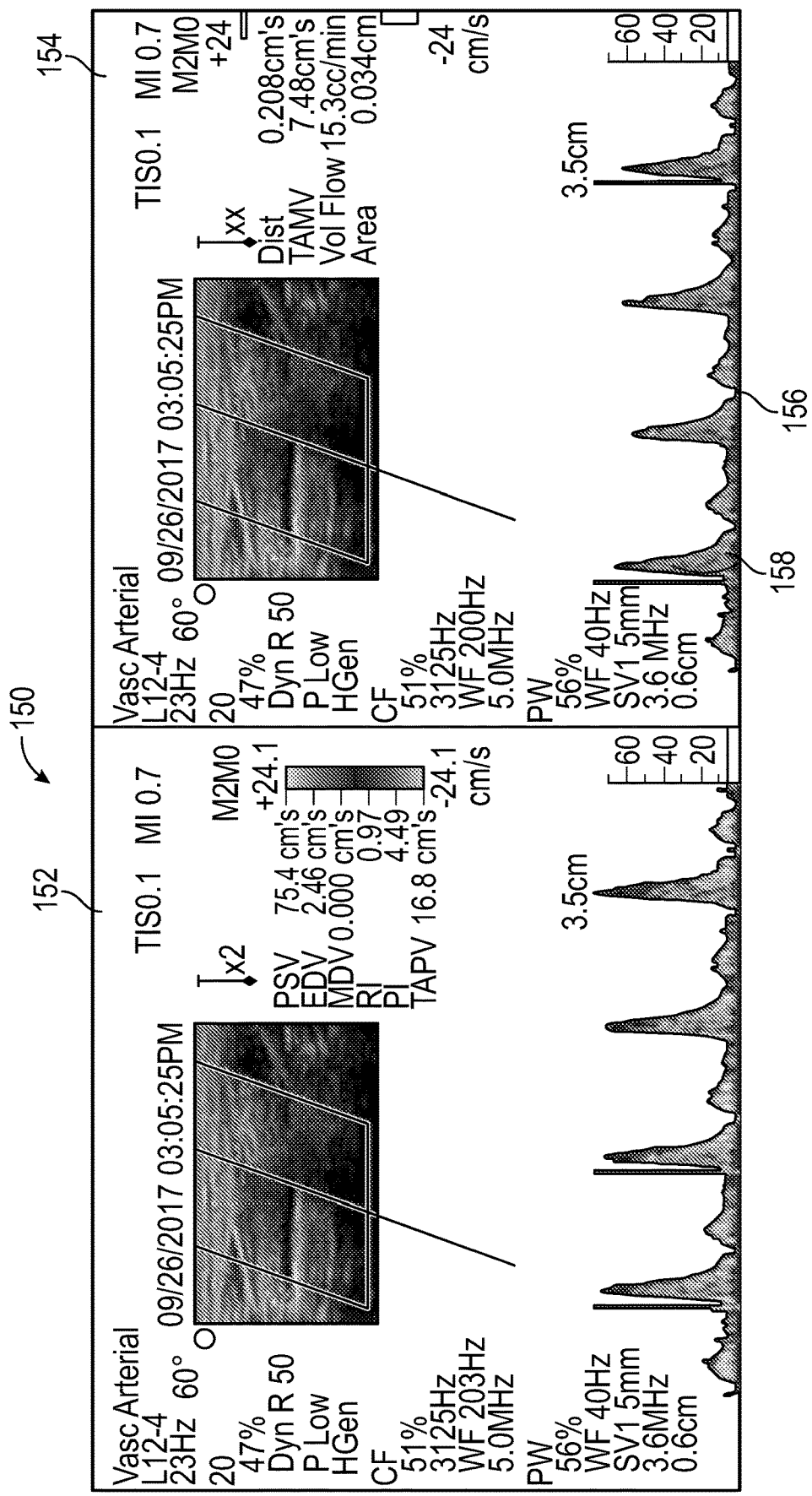
FIG. 1B illustrates a display of example information provided from blood flow monitoring in accordance with various embodiments.

FIG. 1B illustrates a display 150 of example information provided from blood flow monitoring in accordance with various embodiments. FIG. 1B provides information 152, 154, 156, 158 indicative of neuropathy in a test patient, which may include Pulsatility Index (PI), volume flow (VF), and the wave form. In an example, the information may be obtained from probes applied to pressure points 104A, 104B of a human subject, for example at hands and wrists 102A, 102B. While such information is indicative of neuropathy, the use of such information to improve the condition has not been previously contemplated or understood. Particularly, such information 152, 154, 156, 158 is only indicating the condition exists, but does not provide any direction to change the information 152, 154, 156, 158.

Figure 2:
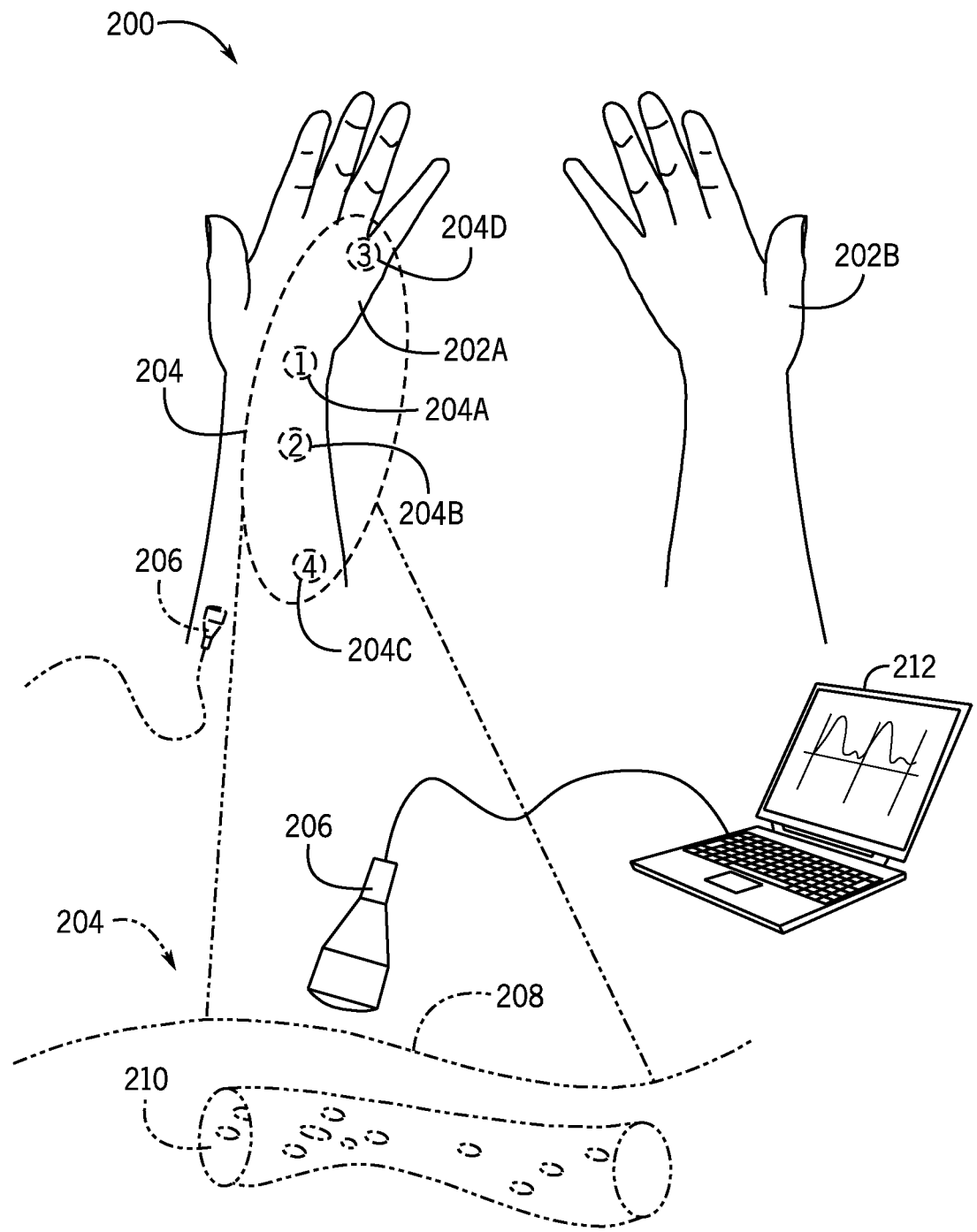
FIG. 2 illustrates an example of computer-supported intraneural facilitation (INF) for vascular changes in accordance with aspects of this disclosure.

In order to resolve the condition demonstrated in FIG. 1A, and to make sense of the information provided in FIG. 1B, the present disclosure utilizes system 200, an embodiment of which is illustrated in FIG. 2. FIG. 2 illustrates an example of computer-supported intraneural facilitation for vascular changes in accordance with aspects of the present disclosure. FIG. 2 illustrates that a human subject with neuropathy may be treated by a series of controlled physical changes to at least two extremities 202A, 202B of the human subject, implemented by a traction device. Although illustrated as hands and wrists 202A, 202B, in other embodiments other extremities, such as legs, ankles, and feet may be targeted, while in still other examples various other portions of the human subject may be targeted, as will be readily understood by one of ordinary skill in the art.

In between each physical change applied to the human subject at extremities 202A, 202B by the traction device, a probe 206 is used to monitor data signals at specific points or areas surrounding the pressure points 204A-D where the physical change is being applied. The signals are processed to identify discriminant features of the collected data, which may include velocity values, among others, as will be readily understood by one of ordinary skill in the art. The discriminant features cluster in a two-dimensional frame, along with a time dimension. Volume Flow (VF) and Perfusion Index (PI) may also be monitored, in addition to the discriminant features. In an example, a physical change applied to the pressure points 204A-D may include manipulating a distal area of the hand 202A. The manipulation may include bending a finger, via the traction device, with reference to points 204A-D. The physical change may be introduced by at least one traction system, and the traction system may be machine-controlled in some examples, or may be controlled by a human operator in other examples. Use of a machine-controlled traction system may allow for application of constant traction at each of reference points 204A-D at all application times and for all subjects. For example, the reference points 204A-D may be stimulated proportional to each other, in order to maintain objective and consistent control of the amount of physical change applied.

Prior to initiating the physical change demonstrated in FIG. 2, a primary physical change may be applied to another part of the body of the human subject. This is demonstrated in the process flow of FIG. 5, for example, and in the system illustrated in FIG. 3. According to an embodiment, once the primary physical change is applied, signals may be obtained from one or more probes at one or more of the points 204A, 204B. Points 204A, 204B may be selected based at least in part on the displayed-out form processing of the received signals. For example, the probes may emit sound waves into the points 204A, 204B, and may receive echoing sound waves through the points 204A, 204B, such as by a Doppler effect. As such, signals obtained from the one or more probes may carry sufficient information that then may be subject to processing via a computer or ultrasound device. Further, as in the case of FIG. 1A, pressure points 204A, 204B may be chosen for their proximity to the area under neuropathy, but also in consideration of the specific indications from the flow pattern, the PI, and the flow volume following the primary physical change. The one or more probes may be, alternatively, applied in areas other than points 204A, 204B, but in proximity to (or in) the particular bodily area of the human subject experiencing neuropathy. The information from the signals can then iteratively be used to adjust the physical change—different from the primary physical change—such that a desired blood flow is pressured into the region experiencing neuropathy. As such, the present disclosure provides methods and systems to drive blood through artery 210 and through related arteries from artery 210 in a staged intervention procedure based on feedback from processing signals that provide blood flow patterns after each stage of physical change, in order to guide a subsequent stage of traction device-implemented physical change.

Figure 3:
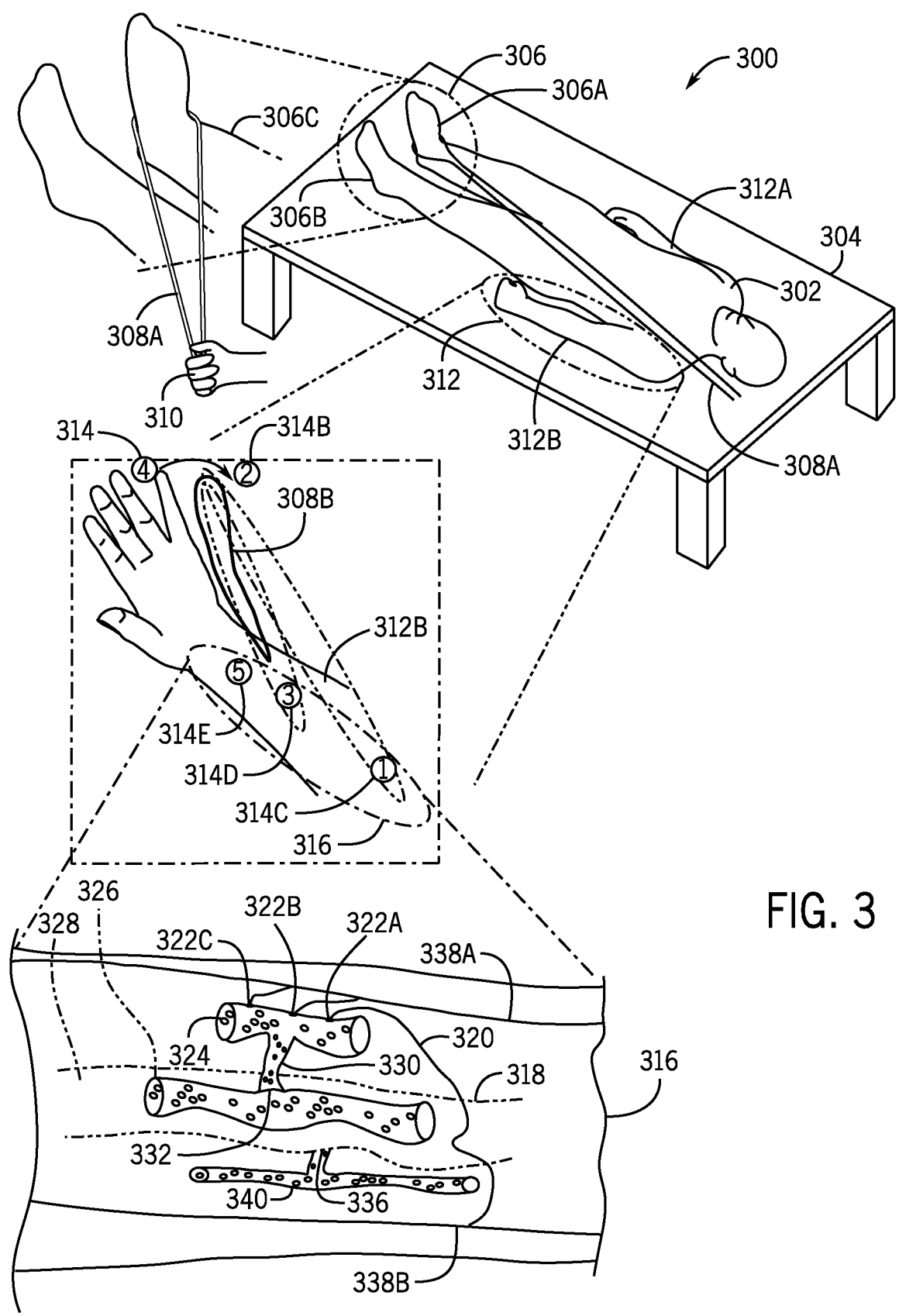
FIG. 3 illustrates further details of a computer-supported INF for vascular changes in aspects of the present disclosure.

FIG. 3 illustrates further details of a computer-supported intraneural facilitation for vascular changes 300 according to various aspects of the present disclosure. As a person having ordinary skill in the art will readily understand, intraneural facilitation induces pressurized blood flow from an artery 324 into circulation in a nervous system of a human subject 302. The circulation referenced herein may be microvascular circulation, according to some embodiments. According to the illustrated embodiment, the microvascular system may be situated around nerves 338A, 338B, and may have two chambers. An outer chamber (or epineurium) 318 is a chamber that regulates blood flow for itself and the inner chamber 340. The outer chamber may be controlled by pressure and hydraulic mechanisms.

In an example, the outer chamber 318 may be directly fed through nutrient or feeding vessels 330 from the larger arteries 324 that bring blood into the outer chamber 318. The continuous flow pushes blood through the outer chamber 318. Feeding vessels 330 are clustered at joints and coiled to allow for movement between the artery 324, 326 and the nerve 338A, 338B, without tearing either tissue. There are also intermittent feeding vessels between the artery and accompanying nerve(s). Inside 328 this outer chamber 318 are smooth arterioles or miniature arteries 326 with smooth muscle, which is innervated by sympathetic nerves 322A-C, 320. While the drawings are for illustration purposes, scale is not presently in consideration in the drawings, and so one of ordinary skill would recognize that arterioles are narrower or smaller than arteries even if drawn at similar sizes in FIG. 3, for instance, The sympathetic nerves 322A-C, 320 are part of the perivascular plexus in the outer chamber 318 that contributes to the hydraulic push of the circulation both in the outer chamber 318 of the nerve and into the inner chamber or endoneurium 340. When the vessels 330 contract, reflux can occur back through the nutrient vessels 330 into the major arteries 324, which can cause circulation to temporarily move in a retrograde fashion.

Once the circulation occurs into the inner chamber 340 of a nerve 338B, such neural flow is controlled electrically instead of hydraulically. While the outer chamber 318 has immediate pressure from blood being fed into it, the inner chamber 340 may not. There is some hydraulic force that propels the inner circulation for the inner chamber 340. Red blood cells in the capillary beds of the endoenurium 340 have a negative charge and are pushed forward in part by the alternating action of a nerve undergoing depolarization and repolarization.

A complex relationship is maintained between red blood cells that are temporarily attracted to a positive charge created by a nerve 322A-322C, 320, 338B undergoing depolarization and surrounding blood cells with a negative charge. The red blood cells (illustrated as oblong-shaped particles in the arteries) that are in the middle of the push and the pull created by the above-referenced charges are released with repolarization of the nerve and accelerated forward due to the release of potential energy. The acceleration creates a temporary increase of pressure and assists with overcoming resistance that may have occurred in the capillary bed while maintaining normal capillary patency. Increased capillary patency promotes normal nerve conduction that occurs within subclinical levels. As such, the nerve conduction is necessary for maintaining tone, providing information to the subconscious about position sense, and other functions.

For a nerve 338A, 338B to trigger or fire, there must be clear connection with the central nervous system (CNS). The connection involves a positive feedback loop with the endoneurial circulation. The better the circulation to the nerve, the better the nerve "depolarizes" or fires and the better the connection is with the central nervous system. This in turn promotes better endoneurial blood flow. Neural control of adjacent arteries is critical for controlling blood circulation in those arteries. A sympathetic plexus 338A partially fed by a local nerve provides a neural induced contraction of smooth muscle in the artery 324. The smooth muscle then tightens, forcing circulation from the feeder vessels 330 into the local nutrient vessels. The nutrient vessels 330 must be patent (open) and the innervated arterioles 326 must also be patent (open) for the nerve 338B to receive circulation locally.

From the above description, there are two systems that work to maintain circulation to the nerves 338A, 338B. Such complex systems provide far-ranging responses to muscle tone that may not be recognizable without the multiple signal processing requirements functioning as feedback in between applied physical changes. Indeed, the signal processing requirements do not merely indicate an issue of flow at the point of application of the probes, but provide a flow pattern indicative of possible redirection that may be administered by additional physical changes that are objectively based on the turning applied to a distal area with respect to reference points in the region of the distal area.

The outer chamber 318 is a holding and regulatory chamber, and is driven hydraulically. The inner chamber 340 is driven electrically. The outer chamber 318 is fed via nutrient vessels 330, while the inner chamber 340 is fed via the outer chamber 318 from an internal portion 328 to a mouth 336 of the inner chamber. In an example, the outer chamber 318 is controlled via a perivascular plexus while the inner chamber 340 is part of a positive feedback loop that includes endoneurial circulation, functioning nerves 338B, and an intact connection with the central nervous system (CNS). The outer chamber 318 and inner chamber 340 of any nerve are part of the greater microvascular circulation and participate in a closed system. The outer chamber 318 has blood constituents and provides hydraulic pressure to local circulation of a nerve 338B. The nerve 338B must have circulation within the chamber 318 to function normally with a symbiotic relationship between a functioning nerve and local blood flow. Neural conduction requires an intact connection to the CNS or normal nerve conduction, otherwise circulation will stall.

Every nerve 322A-C, 320, 338B is fed through capillary circulation of five pathways or tracks. Such pathways or tracks include dural, autonomic, perivascular, spinal, and cutaneous pathways or tracks. As used herein, track 1 refers to the dural track, track 2 refers to the autonomic track, track 3 refers to the perivascular track, track 4 refers to the spinal track, and track 5 refers to the cutaneous track. The type of physical changes and the traction system application are then dependent on the track selected for manipulation. Circulation to both chambers 318, 330 of any nerve will at some point be regulated and will flow through capillaries from each pathway. Each pathway has a primary area where the nerves are more strongly influenced. For example, the fifth cranial or trigeminal nerve (also referred to as the Cranial $5^{th}$) is a primary nerve area influenced by the dural circulation. In another example, the viscera area is influenced by the autonomic pathways or tracks, the radial artery is influenced by the perivascular pathways or tracks and muscle stretching for spinal nerves, and skin innervation is influenced by the cutaneous pathways or tracks.

Two systems are important for maintaining circulation for each nerve as noted elsewhere in this disclosure. The hydraulic system and the electrical system provide controls where applicable in the artery 324 and within the inner chamber 340. With regard to autonomic neuropathy, baroreceptors with defects have been determined to create widespread neuropathy. Baroreceptors may be damaged through autoimmune processes. The baroreceptors ensure pressure is maintained with consistent sympathetic tone so circulation does not pool in abdomen or lower extremities when the human subject is standing. When the baroreceptors are not functioning as intended, widespread neuralgia may occur, during which distal nerves may under-perfuse and neural blood pressure may not be maintained.

Nerve pathology can involve an occurrence at a local micro level, through inflammation or damage to either the outer or inner chambers 318, 340. Nerve pathology can involve dysregulation of arteries 324 that are pushing circulation into the nerve 322A-C, 320, 338B. Nerve pathology can involve neural ischemia of the small nerves 322A-C that innervate arterioles 326 inside the outer chamber 318 and fail to push circulation through nutrient vessels 330. Such circulation failure may be in a forward direction, through arterioles 326 or into the inner chamber 340 through transperineurial vessels 336. Nerve pathology can involve an electrical disconnect at the CNS level, creating nerve and vascular slowing. Nerve pathology can also involve primary areas with any or each of the above-referenced five nerve tracks, thereby creating a patterned slowing of the circulation originating in primary track areas and promoting additional distal neural ischemia. As such, nerve pathology may include dysfunction in the neural baroreceptors creating CNS neural ischemia and under perfusing the capillary beds that are most distal.

According to an embodiment, the present INF method and system initiates treatment by pressurizing or biasing circulation into the nervous system. This may occur after a first step of receiving first signals from a probe at a first area of a human subject to determine a condition requiring treatment, such as neuropathy in the first area. The first signals are processed to provide a first two-dimensional (2D) flow pattern associated with blood flow from a first artery to a second artery supplying at least one nerve of the human subject. The first 2D flow pattern supports the determination of the condition requiring treatment. According to an embodiment, the method can include initiating a first physical change in the first area of the human subject. This may be achieved by turning a joint as far as the human subject is comfortable with, but may also be defined by the use of a traction system 308A that has limiting capabilities. The physical change may be provided in order to control the blood flow to the first area for a first predetermined period of time. For example, the nerve can be pulled along with the accompanying artery as a result of the first physical change. This is demonstrated in the change of position of foot 306 from a first foot position 306A to a second foot position 306C. The subject's other foot 306B remains as initially placed. The traction may be controlled by machine or by hand. In the machine-based control, a feedback loop may be applied by a computer as part of the system offering INF to limit the amount of traction. Control by hand may rely on the material used in the traction control 308A, such that no excessive amount of traction can be applied—e.g., by elastic limitation that absorbs excess traction and does not translate traction to the foot 306C.

With this first physical change, the coiled nutrient vessels are straightened, thereby biasing blood flow from an artery into the outer layer of the nerve within the larger opening in the artery. The pressurized blood flow enables pressure points, and stretches and holds to both induce the more consistent circulation into the inner chamber of nerves that is desired, and also specifies which supplying track of nerves will be used to vacuum or suck the circulation up through the use of Bernoulli's principle. At this time, second signals may be obtained from a probe connected to a blood flow display apparatus comprising a memory including instructions and a processor for processing the instructions. Various components, including a classifier, a display, a controller, and a microprocessor are provided for processing the second signals. For example, the second signals from the probe are processed after causing the first physical change to provide a second 2D flow pattern associated with the blood flow in the first area of testing. The second 2D flow pattern demonstrates a reduction in the blood flow through the second artery.

A secondary hold may be used to identify secondary nerves to bias. Particularly, the secondary hold causes second physical changes in one or more second areas of the human subject. As in the case of the first physical change, the second physical change is provided to control the blood flow for a second predetermined period of time. In an example—as illustrated in FIG. 3—the second physical change is implemented by way of a second traction control system 308B that has three or more reference points for a distal area change. A little finger of human subject 302 is subject to the second physical changes from position (4) 314A to position (2) 314B. Traction control system 308B is applicable to provide reference changes in the second predetermined period of time—either to hold the finger at a reference position (5) 314E, reference position (3) 314D, or reference position (1) 314C. In this example, the ulnar artery next to the ulnar nerve is monophasic; no circulation is going into the nerve from the artery due to local nerve ischemia and increased resistance, pushing the blood flow out.

With the second physical changes 314A-314E, third signals are obtained from the probe. The processing of the third signals provides a third 2D flow pattern associated with the blood flow. The third 2D flow pattern demonstrates an increase in the blood flow through the second artery. Even with the increase in the blood flow, the third 2D flow pattern on an ultrasound (relying on processing the second signals) also reveals poor control of the artery indicating diminished control of the artery with weaker force due to a drying out of the circulation controlling the blood going into the artery, indicating that the nerve is not functioning well and is poorly controlling the accompanying artery. As such, the nerve is not receiving the blood from the nearby artery, which is weakly pushing the blood into the nerve. When it is determined that the third 2D flow pattern requires further improvement to bring circulation through the lymphatics and skin around the left ulnar nerve, the second physical changes may include a further change to bring the circulation through pathways or tracks responsible for the first area. As such, the above INF process maintains the first physical change and the second physical changes for a third predetermined period of time when the increase in the blood flow through the second artery is demonstrated. Once blood is brought through the autonomic nerves in the human subject's organs, the blood is also routed hydraulically or incrementally through the sympathetic nerves of the skin by the additional second physical changes. The first physical change and the second physical changes are released to provide a fourth 2D flow pattern that is different from the first 2D flow pattern—demonstrating improved blood flow in at least the first area, thereby improving the neuropathy condition previously determined in the first area.

In addition to the above first physical change, the second physical changes implemented in one or more second areas of the human subject may be enacted by way of a further physical change in the first area. For example, pressurizing the blood flow in the entire outer nervous system may be provided by controlling the traction control system 308A. This may include pulling 310 the foot of the human subject with a strap 308A to further turn the foot in position 306C, according to an embodiment. In some embodiments, the human subject 302 is prostrate on a supporting fixture 304 while the treatment is administered. Further physical changes may be implemented by placing one or more rolled towels or bolsters under the spine. These rolled towels may enable pressurized blood flow to move in a circular fashion or in a positive feedback loop within the sympathetic nerves that innervate the vertebral joints. The second physical changes may create suction within the capillaries associated with the nerves of the autonomic system. The determination to provide these additional second physical changes is a specific result of the feedback received from the signals processed after each physical change and after specific indicators obtained from the signals—the PI, the peaks, the flow volume, and the velocity points—either receding or approaching.

In addition or alternatively to the towels, the foot turns, and the distal finger stretches, the second physical changes may be implemented by a bolster positioned under the back of the head of the human subject and weighted ankle weight traction system attached to a head area of the human subject. The weight may be a one-pound weight attached to the forehead area, according to an embodiment. This would deform the main nerves that innervate the dura, allowing pressurized circulation to move through this vascular tract (to help with venous circulation, for example). Circulation for all other pathways and tracts will be biased towards the two tracks described herein. This provides an accelerated positive feedback loop and creates a reduction in pressure, while increasing the blood velocity in the capillaries. Further, as to the first and the second physical changes, there may be further adjustments by alternating sub-holds or pressure points applied to the human subject in two tracks that are not biased. These adjustments may help to vary the direction of the circulation that is being drawn into track 1 and track 2. The secondary hold or second physical changes may be provided at a treatment area that is in the most distal skin area innervated by the ulnar nerve. For example, depending on the flow patterns from the probe signals that define tone changes in fingers or hand, when the supporting tracks and fingers go weak or limp, the second physical changes may additionally involve a sequence closer to the organs where the circulation is stronger.

Once the muscle tone changes have improved proximally dependent on the third 2D flow pattern, attention may be redirected to the original secondary hold that defined a first one of the second physical changes. The intent is to determine whether the circulation has been restored to the original secondary hold. The INF system and method herein also incorporate a sensory system to support the traction and intervening signaling aspects—such as by use of palpation and muscle changes. When improvement is not shown, other tracks, such as the viscera, may be checked to determine whether circulation is coming down through the skin. Once checked, the changes next to the organs are monitored as part of the second 2D flow pattern, and when there is an indication of better flow, the second physical changes may be addressed. This process, in essence, opens the circulation improvement aspect of INF closer to an intended goal of circulation in at least the skin area. As such, the sensory system support is provided by monitoring muscle tone changes and swelling reduction. Further, when there is partial resistance with the toes, and swelling is decreased in an area of concern or the area of the secondary hold (i.e., where at least one of the second physical changes is applied), then the ultrasound may be repeated to confirm the fourth 2D flow pattern (e.g., showing improved flow) that is different from the first 2D flow pattern (e.g., decreased or no flow condition).

FIG. 4 illustrates an example 400 of various blood flow patterns and related information 402-416 in a computer-supported intraneural facilitation for vascular changes in accordance with aspects of this disclosure. In the graphical user interface (GUI) of FIG. 4, two aspects of the present INF method are provided. In the GUI display, neural control of arteries occurs by the processed signal points above the horizontal line 418. Neural receptivity of arterial circulation occurs below the line 418. Sympathetic neural ischemia changes the wave form to reduce the sharpness at the peak of the wave form. The PI value 402 is noted as information values or measures provided as a degree of sympathetic control over the amount of blood that is flowing through the artery at that time. The volume flow 404 measures the amount of blood pulsing through the artery. A high volume flow amount indicates adjacent neural resistance with the smaller arterioles in nerves not receiving blood flow. A low PI and a high volume flow are common with patients that have a monophasic wave form. As such, the top two quadrants of the four quadrant display provide blood flow patterns and related information before the INF treatment. Reference numeral 402 provides a low PI value (4.48), and reference numeral 404 provides a low flow volume (15.3 cc/min), while the wave form demonstrates reduced peaks in reference numeral 406 and demonstrates one to none neural receptivity of arterial circulation 408 occurring below the line 418. This neural receptivity of arterial circulation may be a result of receding velocity values implying velocities picked up by the probe as receding away from the probe, while velocities above the horizontal line are velocities picked up as moving towards the probe. As such, a person of ordinary skill would recognize that the receding velocity and increasing velocity values are only provided to distinguish the two types of clustering of velocity data received from the probe.

In contrast, the lower two quadrants of the four quadrant display provide blood flow patterns and related information after or during the INF treatment. Reference numeral 414 provides a higher or improved PI value (9.74), and reference numeral 412 provides a lower or improved flow volume (7.10 cc/min), while the wave form demonstrates prominent peaks in reference numeral 410 and demonstrates at least more than two neural receptivity of arterial circulation 416 occurring below the line 418, according to the illustrated embodiment. The decreased volume flow 412 demonstrates that the flow pattern 410 is indicative of improved circulation going into the nerves as compared with the high circulation 408 that was not going to the nerves.

Figure 5:
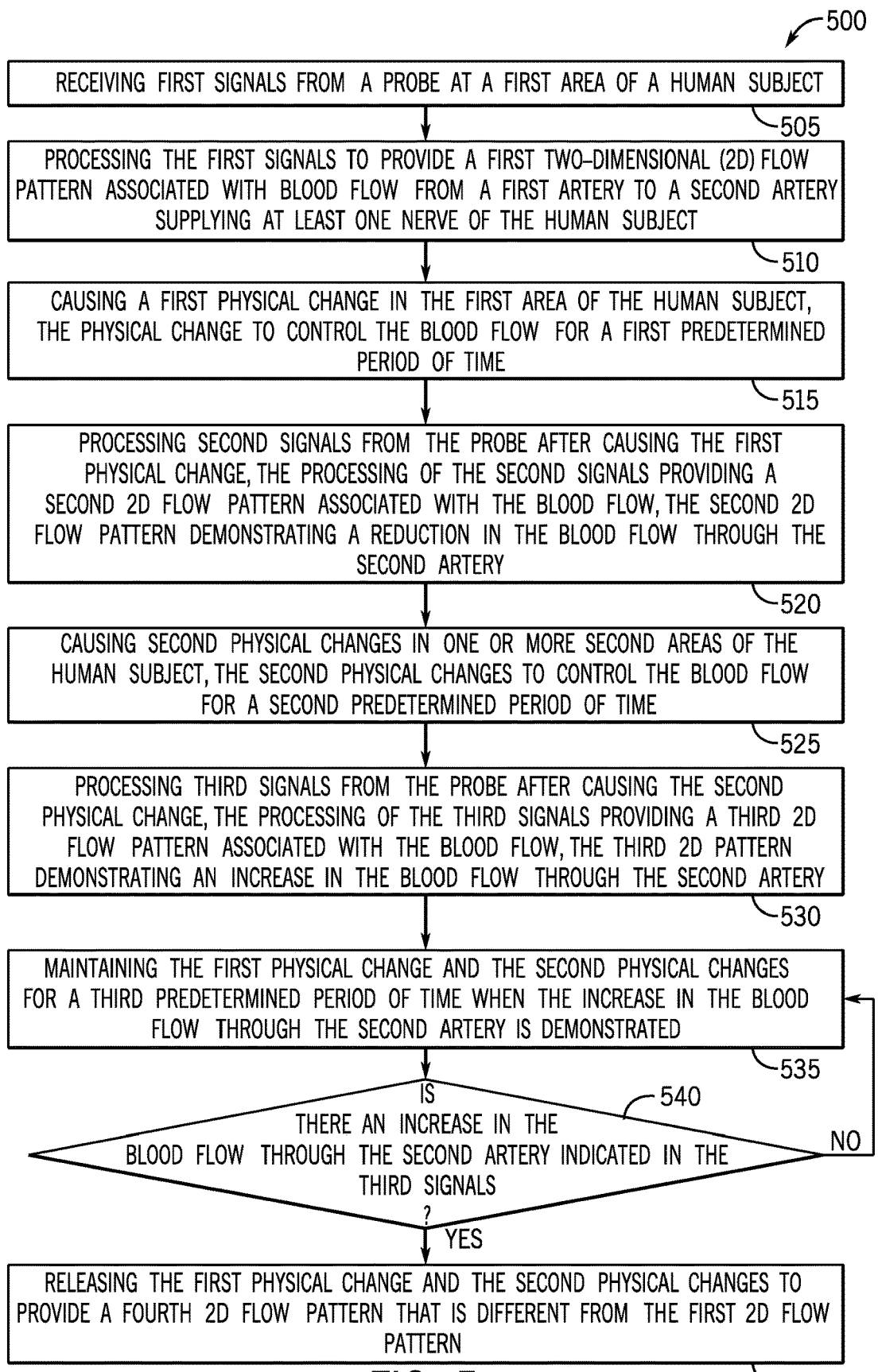
FIG. 5 illustrates an example method of computer-supported INF for vascular changes, in accordance with aspects of this disclosure.

FIG. 5 illustrates an example method 500 of computer-supported intraneural facilitation for vascular changes, in accordance with aspects of this disclosure. The computer-implemented method includes sub-process 505 for receiving first signals from a probe at a first area of a human subject. In sub-process 510, the first signals are processed to provide a first two-dimensional (2D) flow pattern associated with blood flow from a first artery to a second artery supplying at least one nerve of the human subject. Such a process may include identifying discriminant features from the first signals. The discriminant features may be velocity values clustering in a two-dimensional plane, according to an embodiment. Sub-process 515 may include causing a first physical change in the first area of the human subject. For example, the physical change can include turning a foot joint of the human subject to control the blood flow in the area of the foot joint for a first predetermined period of time. Sub-process 520 can include processing second signals from the probe after causing the first physical change. As in the case of the first signals, the processing of the second signals provides a second 2D flow pattern associated with the blood flow. The second 2D flow pattern demonstrates a reduction in the blood flow through the second artery, according to the illustrated embodiment.

The data from the second 2D flow pattern is useful in sub-process 525 for causing second physical changes in one or more second areas of the human subject. For example, a distal area, such as a finger of the human subject, may be subjected to the second physical changes. The second physical changes are enacted in order to control the blood flow for a second predetermined period of time. Sub-process 530 may include processing third signals from the probe, after causing the second physical change. The processing of the third signals provides a third 2D flow pattern associated with the blood flow. The third 2D flow pattern demonstrates an increase in the blood flow through the second artery, according to the illustrated embodiment. In sub-process 535, the first physical change may be maintained, along with the second physical changes, for a third predetermined period of time. This can increase the blood flow through the second artery as demonstrated from the third 2D flow pattern. In an example, as noted with reference to FIG. 4, the decrease in the flow volume, along with the PI information and the wave form pattern, are indicative of the increase in blood flow through the second artery. Sub-process 540 verifies the increase in the blood flow through the second artery as per the third signals. Once confirmed, sub-process 545 includes releasing the first physical change and the second physical changes to provide a fourth 2D flow pattern that is different from the first 2D flow pattern and that confirms that the neuropathy is managed. In the event that the increase in blood flow is not confirmed, then the maintenance sub-process 535 continues until increase in blood flow is observed sufficient to proceed to sub-process 545 and release the first and second physical changes.

The INF treatment discussed throughout this disclosure ensures that neural problems, including impaired, sympathetic control of arteries with weak pressure into neural arterioles, and inflamed neural arterioles, are addressed. In effect, the INF treatment uses the specific and directed traction control systems with intervening signal verification to bring blood flow out of artery and into sympathetic nerves, thereby controlling the artery that is extrinsic to the artery and nerve. This creates a vascular pathway from organs to peripheral nerves in skin through the sympathetic nerves in the skin. The intervening signal data could be transmitted to a classifier or an ultrasound machine, such as a Doppler ultrasound. The signals are processed to determine flow volume, PI, and wave forms for classification above or below the horizontal line and to provide information from the peak shape of the wave form. Blood flow in the artery with poor arterial contractility and decreased neural receptivity of circulation is improved, thereby to improve arterial contractility and increase neural receptivity of circulation.

Figure 6:
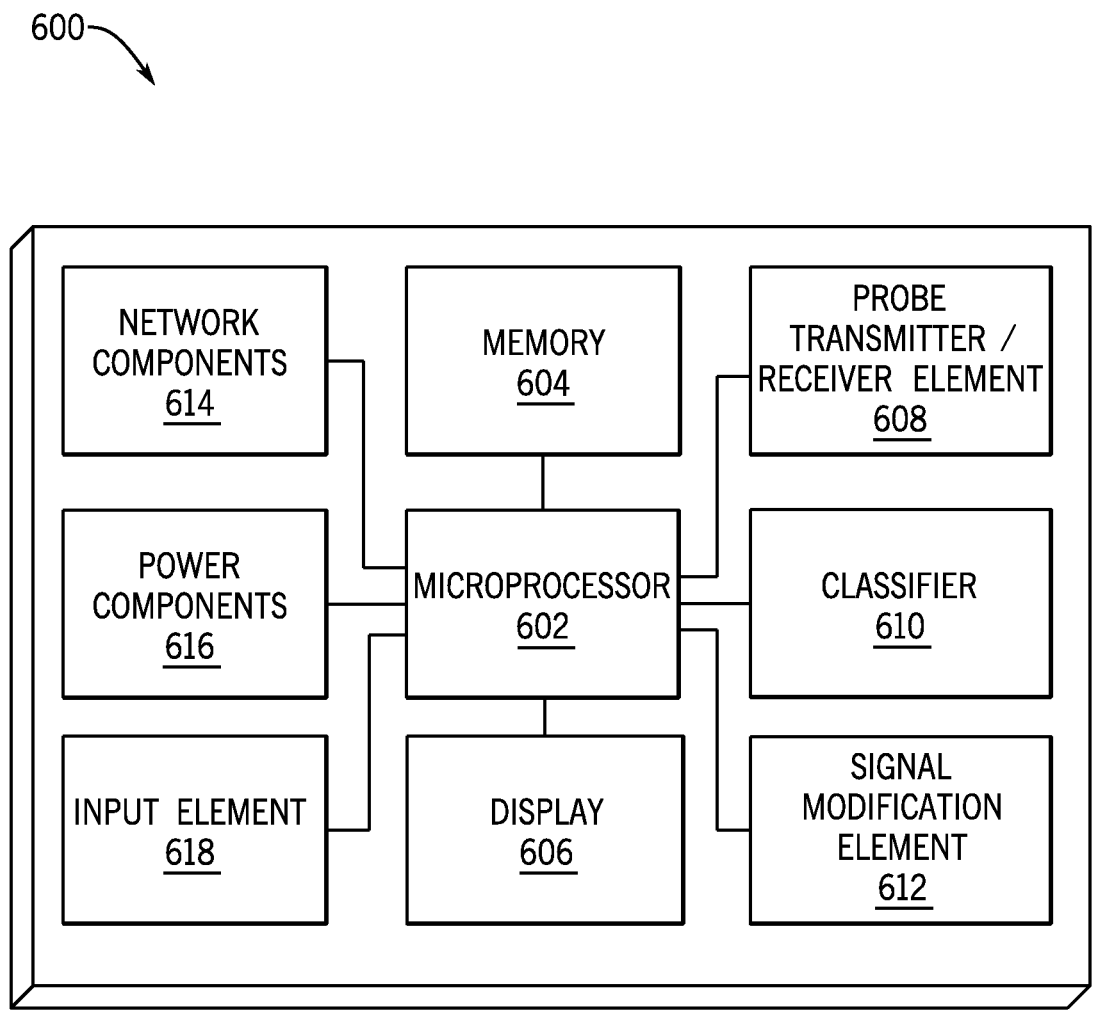
FIG. 6 illustrates an example device providing a computer-supported INF for vascular changes in a system, in accordance with aspects of this disclosure.

FIG. 6 illustrates an example device 600 providing a computer-supported intraneural facilitation for vascular changes in a system, in accordance with aspects of this disclosure. Particularly, an example set of components 602-618 are provided in the device 600. As such, device 600 may be device 212 in the example of FIG. 2, according to an embodiment. In an example, the device 600 may be an ultrasound machine with developed capabilities based on the present disclosure. For example, the developed capabilities enable the ultrasound machine to identify and process discriminant features from each of the first, second, third, and fourth signals referenced in prior examples. As such, the ultrasound machine 600 includes instructions in memory 604 for the microprocessor 602, classifier 610, and signal modification element 612 to generate or provide discriminant features from each of the first, second, and third signals. The discriminant features in each of the first, second, and third signals may include velocity values clustering in a two-dimensional plane to support a determination that a neuropathy issue is identified and is being managed.

The illustrated example device 600 includes at least one main microprocessor 602 for executing instructions stored in physical memory 604 on the device, such as dynamic random-access memory (DRAM) or flash memory, among other such options. As would be apparent to one of ordinary skill in the art, the device 600 can include many types of memory, data storage, or computer-readable media as well, such as a hard drive or solid state memory functioning as data storage or memory 604 for the device. Application instructions for execution by the at least one microprocessor 602 can be stored by an extra data storage (separate from memory 604), that is then loaded into memory 604 as needed for operation of the device 600. The microprocessor 602 can have internal memory, as well, to be used in some embodiments for temporarily storing data and instructions for processing. The device 600 can also support removable memory (as part of or separate from memory 604) useful for sharing information with other devices. The device may also include one or more power components 616 for powering the device. The power components can include, for example, a battery compartment for powering the device using a rechargeable battery, an internal power supply, or a port for receiving external power, among other such options, as will be readily understood by one having ordinary skill in the art.

The computing device may include, or may be in communication with, at least one type of display element 606, such as a touch screen, organic light emitting diode (OLED), or liquid crystal display (LCD). Some devices may include multiple display elements, and may also include LEDs, projectors, and the like. The device can include at least one communication or networking component 614, and may enable transmission and receipt of various types of data or other electronic communications. The communications may occur over any appropriate type of network, such as the Internet, an intranet, a local area network (LAN), a 5G or other cellular network, or a Wi-Fi network, or can utilize transmission protocols such as BLUETOOTH® or NFC, among others. The device can include at least input element 618 capable of receiving input from a user or other source. This input device can include, for example, a button, dial, slider, touch pad, wheel, joystick, keyboard, mouse, trackball, camera, microphone, keypad, or other such device or component. Various devices can also be connected by wireless or other such links as well, in some embodiments. In some embodiments, a device might be controlled through a combination of visual and audio commands, or gestures, such that a user can control the device without having to be in contact with the device or a physical input mechanism. In addition, the device 600 can include a probe transmitter/receiver element 608 for providing and receiving signals, such as Doppler audio signals. In an operative example, Doppler signals also may be converted to audio signals, with higher velocities of blood flow providing high-pitched sounds, while lower velocities provide low-pitched sounds. The classifier 610 may be a neural network classifier for classifying discriminant features of the audio signals—or directly from the Doppler audio sounds. The discriminant features may be Fourier transformed audio signals or non-transformed velocity values as presented from the audio signals.

Figure 7:
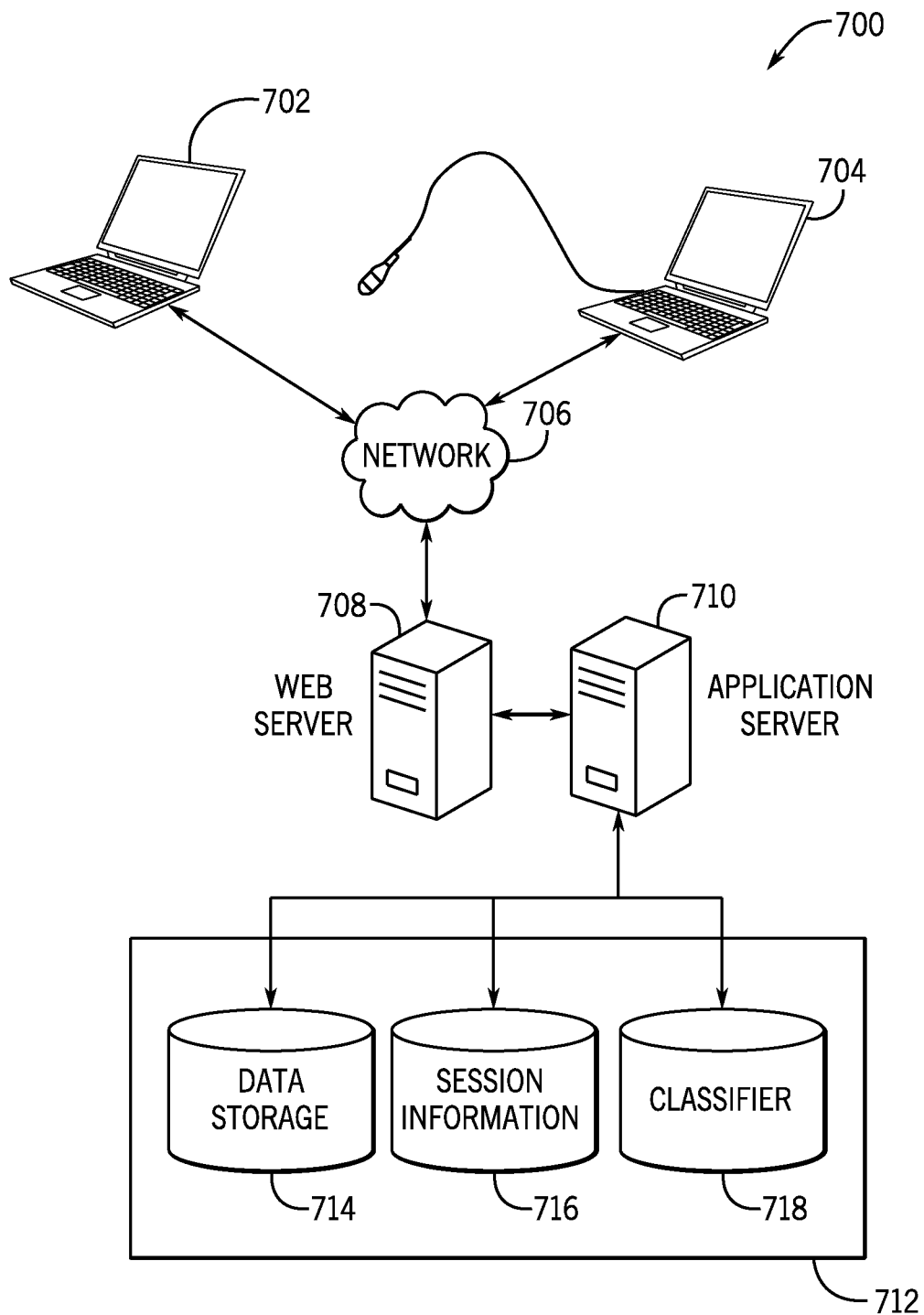
FIG. 7 illustrates an example network architecture used in a system for computer-supported INF for vascular changes, in accordance with aspects of this disclosure.

Much of the functionality utilized with various embodiments may be operated in a computing environment that may be operated by, or on behalf of, a service provider or entity. Alternatively, or in addition, there may be dedicated computing resources or resources allocated as part of a cloud environment. FIG. 7 illustrates an example network architecture or environment 700 used in a system for computer-supported intraneural facilitation for vascular changes, in accordance with aspects of this disclosure. In addition, the example network architecture or environment 700 may be used to share the INF treatment process or to control the INF treatment process remotely. The resources can utilize any of a number of operating systems and applications, and can include any number of workstations or servers 702, 704. Various embodiments may utilize at least one cloud or internet-based network 706 for supporting communications using any of a variety of commercially-available protocols, such as TCP/IP or FTP, among others. Other example networks 706 include, for example, a local area network, a wide-area network, a virtual private network, the Internet, an intranet, and various combinations thereof. The servers 712 may be used to host an offering such as portions of the classifier 610. This allows retraining of the classifier to provide a testing neural network or a training neural network for improving system accuracy. In an example, once the wave forms are identified for a patient with the condition, the wave form values or points are stored to train the network. Once INF treatment is administered, the wave form improvements are provided in the form of new values or points that can be used to train a second network. Then, for future human subjects, the human subject is tested against the two networks to determine where the wave form obtained from each future human subject classifies. When the classification is indicative of normal blood flow patterns, then a condition of the human subject is determined as positive and not requiring treatment. Further, if the classification is indicative of a neuropathy condition existing, then the human subject is administered the INF treatment until at least the third signals retrieved after the second physical changes classify in the second network.

As the neural network process is a complex data intensive process, the classifier or portions of the classifier 718 may be operational from servers 712. Data for each session of the INF treatment may be encrypted and stored in data storage 714 with anonymity but for indications of severity of the condition. The session information 716 is useful for ongoing INF treatments, and the data may be moved from the session information 716 to the data storage 714 after the session is complete. The data then may be moved to the classifier to improve the classifier 718. In an example, apart from neural networks, support vector machines (SVM) or k-nearest neighbor algorithms may be used. As with the case of the neural network, pitch or other features, including Fourier transforms and linear predictive coefficients, may be extracted from audio versions of the received signals from the probe. These features are used to train or classify data into clusters.

The functions performed by the servers 708, 710, 712 may be enacted by instructions configured to execute programs or scripts in response to requests from user devices 702, 704. Such a process may include executing one or more applications that may be implemented as one or more scripts or programs written in any appropriate programming language. The server(s) 708, 710, 712 may also include one or more database servers for serving data requests and performing other such operations. The environment 700 can also include any of a variety of data stores and other memory and storage media as discussed above. Where a system includes computerized devices, each such device can include hardware elements that may be electrically coupled via a bus or other such mechanism. Example elements include, as discussed previously, at least one central processing unit (CPU) and one or more storage devices, such as disk drives, optical storage devices, and solid-state storage devices such as random access memory (RAM) or read-only memory (ROM), as well as removable media devices, memory cards, flash cards, etc., as will be readily understood by one of ordinary skill in the art. Such devices can also include or utilize one or more computer-readable storage media for storing instructions executable by at least one processor of the devices. An example device may also include a number of software applications, modules, services, or other elements located in memory, including an operating system and various application programs. It should be appreciated that alternate embodiments may have numerous variations from that described above.

Various types of non-transitory computer-readable storage media can be used for various purposes as discussed and suggested herein. This includes, for example, storing instructions or code that can be executed by at least one processor for causing the system to perform various operations. The media can correspond to any of various types of media, including volatile and non-volatile memory that may be removable in some implementations. The media can store various computer readable instructions, data structures, program modules, and other data or content. Types of media include, for example, RAM, DRAM, ROM, EEPROM, flash memory, solid state memory, and other memory technology. Other types of storage media can be used as well, as may include optical (e.g., Blu-ray or digital versatile disk (DVD)) storage or magnetic storage (e.g., hard drives or magnetic tape), among other such options. Based on the disclosure and teachings provided herein, a person of ordinary skill in the art will appreciate other ways and/or methods to implement the various embodiments.

The environment in FIG. 7 may be, in one embodiment, a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are described. Thus, the depictions of various systems and services herein should be taken as being illustrative in nature, and not limiting to the scope of the disclosure.

Various aspects can be implemented as part of at least one service or web service, such as may be part of a service-oriented architecture. Services such as web services can communicate using any appropriate type of messaging, such as by using messages in extensible markup language (XML) format and exchanged using an appropriate protocol such as SOAP (derived from the "Simple Object Access Protocol"). Processes provided or executed by such services can be written in any appropriate language, such as the Web Services Description Language (WSDL). Using a language such as WSDL allows for functionality such as the automated generation of client-side code in various SOAP frameworks.

In embodiments utilizing a server, the server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python®, or Tool Command Language (TCL), as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices may also include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

The vascular limitations imposed on a single neuron are complex and involve multiple systems that participate in regulating and promoting neurovascular circulation distally and proximally. These systems may have a compromised vascular system distally or locally which may impact the circulation both locally and distally through hypofunction or hyperfunction of the regulatory system both proximally and distally.

Ultrasound imaging is critical to identifying which systems are compromised either proximally or distally and which nerves have been impacted around an ultrasound probe. As such, ultrasound imaging identifies the systems that impact the neural circulation being targeted and the level of ischemia that is occurring at neurovascular structures proximal to the ultrasound probe.

According to an embodiment of a computer-implemented method for administering INF treatment, the method includes receiving first signals from a probe at a first area of a human subject. The method further includes processing the first signals to provide a first two-dimensional (2D) flow pattern. The first two-dimensional (2D) flow pattern provides information as to which neurovascular structures are most impacted and which regulatory systems, either local or distal, need to be addressed. Ultrasound imaging with analysis of wave form and pulsatility provides guidance to INF as to where the treatment should commence.

INF provides two specific options in treating neuropathic pain. The options are: (1) determining which neural structures are the most impacted and in need of a treatment, and (2) determining which vascular systems need to be addressed that prevent circulation from reaching a specific area. For example, if the wrong nerves are targeted, then the capillaries may remain closed as the nerves impacted have been ignored in favor of less deserving ischemic sites. If the wrong track systems have been targeted, therefore, the vascular tracks responsible for a particular nerve's circulatory lack will remain closed or dysfunctional with a potential for the reversal of the treatment process.

Below is a table that describes four ultrasound readings at a vascular site.

TABLE 1

| Area of Graph | Function Assessed | Normal at peripheral vessels | Vascular Tracks Assessed | Dysfunction Indicates |
|---|---|---|---|---|
| Anterograde Pulsatility index (PI) | Sympathetic control of local artery from nerve | 8-10 PI | Primarily 1-3 neutral | Neural ischemia of paravertebral ganglion and insular cortex |

TABLE 1-continued

| Area of Graph | Function Assessed | Normal at peripheral vessels | Vascular Tracks Assessed | Dysfunction Indicates |
|---|---|---|---|---|
| Anterograde Volume flow (VF) | Large vessel circulation coming into local artery | Varies. Popliteal, anterior tibial artery over 100 cc/min, distal posterior tibial artery, peroneal artery 8-10 cc/min | 2-4 in neutral | Low indicates autoimmune condition decreasing volume flow, higher indicates local capillary closure. |
| Retrograde pulsatility index (PI) | Distal cutaneous receptivity to circulation | 8 to 10 PI | Primarily 4,5 of skin | Immediately distal cutaneous and sympathetic ischemia |
| Retrograde volume flow (VF) | Distal nerve trunk circulation | ⅓ to ¼ of anterograde | 2-4 of muscle | Immediately distal to probe nerve trunk ischemia |

The top part of the ultrasound graph is called anterograde. Anterograde describes the contractility of the vessel and the total volume flow coming into sight of the ultrasound. The ultrasound views circulation moving away from the ultrasound in the artery.

The bottom part of the ultrasound graph describes the volume flow coming back into view of the ultrasound on the artery after the circulation has entered the nerve. Further, the bottom part of the ultrasound graph describes the pulsatility of the flow that returns into the view of the ultrasound. The bottom part of the graph may provide the most reliable indication regarding the receptivity of the neural capillaries to circulation from the artery.

The volume control of the artery by the nerve (as seen in the top of the ultrasound graph with anterograde wave form with PI and volume flow) and neural receptivity of the circulation coming into neural capillaries (as seen by retrograde waveform analysis with volume flow and pulsatility index) provide useful information regarding neural ischemia in neural structure circulation and oxygenation. Neural ischemia is unique and critical to neuropathy treatment. Decreased anterograde pulsatility reflects the extent neural control of sympathetic nerves and the viability of the insular cortex impacting the circulation at the site of the ultrasound probe. Increased volume flow at the site of the ultrasound probe may indicate that the nerve neurovascular vessels capillary have closed such that there is increased volume flow at the site of the ultrasound head, with the circulation remaining in the artery. Decreased volume flow at the site of the ultrasound probe may indicate histamine release with immune activation and reduced hydraulic pressure into nerve capillary beds.

According to an embodiment of the present disclosure, the aforementioned ultrasound readings may be used to determine the most compromised nerve system and requirements for a treatment. Further, ultrasound readings may be transmitted to a statistical program as described in embodiments of the present disclosure. The statistical program may generate data for each pertinent system that impacts the nerves being assessed (the nerves directly below the transducer placement). Higher numbers may indicate more nerves requiring INF treatment.

With ultrasound guidance, INF may address major lower extremity nerves, upper extremity nerves, and nerve roots as illustrated in TABLE 2 below.

TABLE 2

| Position of transducer | Vascular structure evaluated | Neural structure evaluated |
|---|---|---|
| Medial ankle | Distal posterior tibial artery | Tibial nerve |
| Lateral ankle | Distal peroneal artery | Peroneal nerve |
| Popliteal fossa | Popliteal artery | Tibial and peroneal nerve |
| Upper thigh | Femoral artery | Femoral nerve |
| Posterior thigh | deep femoral artery | Sciatic nerve |

A statistical program may be used to analyze all components of the ultrasound readings and produce numbers for ischemia. In general, decreased anterograde pulsatility indicates autonomic and dural ischemia.

To address anterograde volume flow issues, INF may need to address neutral clearing with insular treatment. INF strategies may be designed to use subholds to bias a circulation through this system.

Embodiments of the present disclosure can be further understood by reference to the following examples.

Example 1

Statistical Analysis of Anterograde/Retrograde Waveforms

In an embodiment of the present disclosure, a probe is applied to pressure points in a human subject. Pressure points may be chosen for their proximity to the area under neuropathy.

Following the application of the probe to the pressure points of the human subject, an ultrasound machine may be used to process signals received from the probe. The ultrasound machine may provide at least the following information upon processing each of the received signals:
 a. Anterograde PI (AP)
 b. Anterograde volume flow (AV)
 c. Retrograde PI (RP)
 d. Retrograde volume flow (RV)

The above information may be used to determine whether distal or local control causes neuropathy. The information also may be used to determine whether inflammation is in a circulation of nerves distal to the probe or created from nerves proximal to the probe. Consequently, circulation in the neurovascular tissue can be mobilized or shunted and eventually larger vessels will fill additional capillary beds.

While the above information is indicative of neuropathy, the use of such information to improve the condition has not been previously contemplated or understood. Particularly, such information only indicates the condition exists, but does not provide any direction to change the information.

The following calculation example provides those of ordinary skill in the art with specific embodiments of Statistical Analysis of a computer-implemented method for administering INF treatment for vascular change within the scope of the present disclosure:

a. Anterograde PI (AP): 7.16
 b. Anterograde VF(AV): 17.3
 c. Retrograde PI(RP): 3.86
 d. Retrograde VF(RV): 9.02

According to an embodiment of the present disclosure, the computer-implemented method may be used to determine a ratio between distal control (DC) and local circulation (LC). In accordance with the present disclosure, the computer-implemented method may be used to determine distal control (DC) by using Equation (1), where AP represents Anterograde PI and AV represents Anterograde volume flow.

$$DC=\text{sqrt}(AP*AV)$$

$$DC=\text{sqrt}(7.16*17.3)$$

$$DC=11.12 \tag{1}$$

In a specific embodiment of the computer-implemented method, local control (LC) may be determined by Equation (3) where RP is retrograde PI. Equation (2) may be used to determine the difference between anterograde VF (AV) and retrograde volume flow (RV). According to an embodiment of the present disclosure, the ideal retrograde volume flow (RV) should be ¼ of anterograde.

$$RD=AV-RV$$

$$RD=17.3-9.02=8.28 \tag{2}$$

$$LC=\text{sqrt}(RP*RD)$$

$$LC=\text{sqrt}(3.86*8.28)=5.65 \tag{3}$$

A local ratio may indicate the percentage by which local neurovascular circulation is impacting targeted nerves compared to nerves distal the site of the probe that regulate the circulation near the region of the probe.

According to an embodiment of the computer-implemented method, anterograde to retrograde ratio (AR) may be determined by Equation (4).

$$AR=DC/LC$$

$$AR=11.129/5.65$$

$$AR=0.50796 \tag{4}$$

An upper ratio (UR) may indicate the percentage the distal control is greater than the local control. In an embodiment of the present disclosure, the computer-implemented method may be used to determine UR by using Equation (5).

$$UR=(1-AR)+1$$

$$UR=1.49204 \tag{5}$$

According to embodiments of the computer-implemented method, High PI (HP), Low PI (LP), High VF (HV), and Low VF (LV) may be determined by Equation (6), Equation (7), Equation (8), and Equation (9), respectively.

a. High PI (HP)

$$HP=\text{sqrt}(AP*UR/\text{sqrt}(AV*RP*RD)$$

$$HP=\text{sqrt}(7.16*1.492/\text{sqrt}(17.3*3.86*8.28)$$

$$HP=0.65 \tag{6}$$

b. Low PI (LP)

$$LP=\text{sqrt}(RP*LR/\text{sqrt}(AV*AP*RD)$$

$$LP=\text{sqrt}(3.86*0.507/\text{sqrt}(7.16*17.3*8.28)$$

$$LP=0.2474 \tag{7}$$

c. High VF (HV)

$$HV=\text{sqrt}(AV*UR/\text{sqrt}(AP*RP*RD)$$

$$HV=\text{sqrt}(17.3*1.492/\text{sqrt}(7.16*3.86*8.28)$$

$$HV=1.3062 \tag{8}$$

d. Low VF (LV)

$$LV=\text{sqrt}(RV*LR/\text{sqrt}(AV*AP*RP)$$

$$LV=\text{sqrt}(9.02*0.507/\text{sqrt}(7.16*17.3*3.86)$$

$$LV=0.457753 \tag{9}$$

According to embodiments of the present disclosure, the computer-implemented method may be used to determine FCAP, FCAV, FCRP, and FCRV by using Equation (10), Equation (11), Equation (12), and Equation (13), respectively. AP, AV, RV and RP are subtracted from each of their respective norms and AP, AV, RV and RP are then made positive numbers in the calculation.

$$CAP=9-AP$$

$$CAP=9-7.16=1.84$$

$$FCAP=\text{sqrt}(CAP^2)$$

$$FCAP=1.84$$

$$CAV=8-17.3=-9.3 \tag{10}$$

$$FCAV=\text{sqrt}(CAV^2)$$

$$FCAV=9.3$$

$$CRP=8-RP$$

$$CRP=8-3.86=4.14 \tag{11}$$

$$FCRP=\text{sqrt}(CRP^2)$$

$$FCRP=4.14$$

$$CRV=3-RV$$

$$CRV=3-9.02=-6.02 \tag{12}$$

$$FCRV=\text{sqrt}(CRV^2)$$

$$FCRV=6.02 \tag{13}$$

According to an embodiment of the present disclosure, the adjusted numbers, FCAP, FCAV, FCRP, and FCRV may be multiplied by the calculated values of High PI (HP), Low PI (LP), High VF (HV), and Low VF (LV) to determine likelihood ratios LHPI, LLPI, LHVF, and LLVF.

According to embodiments of the present disclosure, the computer-implemented method may be used to determine the likelihood ratios LHPI, LLPI, LHVF, and LLVF by using Equation (14), Equation (15), Equation (16), and Equation (17), respectively.

$$LHPI=(9-FCAP)*HP$$

$$LHPI=(9-1.84)*0.659=4.72 \quad (14)$$

$$LLPI=FCRP*LP$$

$$LLPI=4.14*0.2474$$

$$LLPI=0.707 \quad (15)$$

$$LHVF=(8-FCAV)*HV$$

$$LHVF=(8-9.3)*1.3=-12.09 \quad (16)$$

$$LLVF=(8-FCRV)*LV$$

$$LLVF=6.02*0.45=-2755 \quad (17)$$

According to embodiments of the present disclosure, the computer-implemented method may be used to determine High pulsatility, PHI by using Equation (18).

$$PHI=(9-FCAP)*LHPI/LHPI^2*0.01$$

$$PHI=(9-1.84)*4.72/4.72^2*0.01$$

$$PHI=0.1468=14.68\% \quad (18)$$

In this example, High pulsatility, PHI has a 14.68% deficit.

According to embodiments of the present disclosure, the computer-implemented method may be used to determine High volume, PHV by using Equation (19).

$$PHV=(8-FCAV)*LHVF/LHVF^2*0.01$$

$$PHV=(8-9.3)*-1.6/-1.6^2*0.01$$

$$PHV=2.3227=232.28\% \quad (19)$$

In this example, High volume, PHV has a 232.28% deficit.

Example 2

Ultrasound Guided Administration of INF

The following example provides those of ordinary skilled in the art with specific embodiments of a computer-implemented method for administering INF treatment as used in clinical settings to treat chemotherapy-induced peripheral neuropathy (CIPN) in a human subject, for example at a foot, within the scope of the present disclosure. Chemotherapy-induced peripheral neuropathy (CIPN) often accompanied by pain, tingling, and sensitivity in the hands and feet. According to an embodiment of the present disclosure, a probe is applied to pressure points adjacent the foot of the human subject to obtain information from at least the following arteries:
  a. The posterior tibial artery
  b. The peroneal artery
  c. The popliteal artery Following the application of the probe to the pressure points adjacent the foot, an ultrasound machine may be used to process signals received from the probe. The ultrasound machine may provide at least the following information upon processing each of the received signals.

The signal received from tibia artery and processed by the ultrasound machine may provide the following information:
  a. Anterograde PI: 10.64, anterograde volume flow: 7.70
  b. Retrograde PI: 5.22, retrograde volume flow: 3.64
  c. According to an embodiment of the present disclosure, the above information may be statistically analyzed and may further provide the following information.
     i. High PI deficit: 0.64%
     ii. Low PI deficit: 72.90%
     iii. High VF deficit: 3.83%
     iv. Low VF deficit: 58.94%
  d. The obtained information may provide the following observations. Considering the posterior tibial artery primarily feeds the distal tibial nerve under the foot, the following observations may be derived from the obtained information subject to the statistical analysis:
     i. A minor circulatory deficit through plantar nerves (Low VF)
     ii. A minor to moderate circulatory deficit through plantar the surface of the foot
     iii. A distant control of circulation largely intact (nerve roots, sympathetic nerves)

The signal received from peroneal artery and further processed by the ultrasound machine may provide the following information:
  a. Anterograde PI: 9.64, anterograde volume flow: 7.30 cc/min
  b. Retrograde PI: 5.22, retrograde volume flow 4.91 cc/min
     i. According to an embodiment of the present disclosure, the foregoing information may be statistically analyzed and further provide the following information:
        1. High PI deficit: −1.05%
        2. Low PI deficit: 58.41%
        3. High VF deficit: −4.4%
        4. Low VF deficit: 500.87%
  c. The obtained information may further provide the following observations. Considering the peroneal artery primarily feeds the distal peroneal nerve under the foot, the following observations may be derived from the obtained information subject to the statistical analysis:
     i. Significant under perfusion of motor branches of peroneal nerve (low VF)
     ii. A minor to moderate circulatory deficit through dorsal surface of foot
     iii. A distant control of circulation largely intact (nerve roots, sympathetic nerves)

In an embodiment of the present disclosure, the computer-implemented method may further include causing a first physical change in the first area of the human subject. In this example, the selected first area of the human subject where the first physical change to be caused is on top of the foot where the motor branches of peroneal nerves may be found.

According to an embodiment of the present disclosure, the computer-supported intraneural facilitation induces pressurized blood flow from an artery into circulation in a nervous system of the human subject. In this particular example, the computer-supported intraneural facilitation primary treatment track may include spinal nerves (circulation running through main nerves, not over skin or lymphatics) and perivascular plexus (circulation running through perivascular plexus running through large accompanying arteries).

The primary treatment hold is determined to be muscles that are innervated by the motor branches of the peroneal nerve with those nerves being targeted or "stretched." In this example, extensor digitorum brevis is targeted.

In an embodiment, muscle tone and skin changes according to a predetermined level are monitored to determine the subsequent step in the computer-implemented method for administering INF treatment.

After causing the first physical change in the top of the foot, the second signal from the probe is obtained and processed by the ultrasound machine to obtain information associated with the peroneal artery. Subsequently, the computer-implemented method may be used to generate the following information:
  a. Anterograde PI: 8.86, Anterograde VF: 9.8 cc/min
  b. Retrograde PI: 7.38, Retrograde VF: 3.86 cc/min
  c. According to an embodiment of the present disclosure, the generated information by the computer-implemented method may be statistically analyzed and further provide the following information:
    i. High PI deficit: 1.26%
    ii. Low PI deficit: 4.62%
    iii. High VF deficit: 0.14%
    iv. Low VF deficit: 59.7%

An embodiment of the computer-implemented method may be used to compare the current Low VF deficit value to the previously obtained Low VF deficit value to determine the subsequent step. A decrease in Low VF deficit value towards a predetermined acceptable level may indicate improved blood flow in at least the first area. In this example, the low VF deficit improves from 500% deficit to 59.7% deficit. Therefore, the physical change caused in the first area improves the chemotherapy-induced peripheral neuropathy (CIPN) in the foot of the human subject. Following the improvement in the neuropathy condition, the computer-implemented method for administering INF treatment may be terminated. On the other hand, if the Low VF deficit value does not decrease towards the predetermined acceptable level, the computer-implemented method for administering INF treatment may be repeated by causing second physical changes in one or more second areas of the human subject. For example, the second areas of the human subject where the second physical changes to be caused may be chosen in consideration of the specific indications from the flow pattern, the PI, and the flow volume following the primary physical change.

In this specific example, the second areas may include posterior leg and anterior leg. As such, according to embodiments of the present disclosure, the computer-implemented method provides methods and systems to drive blood through the artery and through related arteries in a staged intervention procedure based on feedback from processing signals that provide blood flow patterns after each stage of physical change, in order to guide a subsequent stage of physical change.

This application is a PCT application and claims priority to, and the benefit of, U.S. Provisional Application No. 62/661,568, filed Apr. 23, 2018, titled "COMPUTER-SUPPORTED INTRANEURAL FACILITATION FOR VASCULAR CHANGES," which is incorporated herein by reference in its entirety.

The present disclosure described herein, therefore, is well adapted to carry out the objects and attain the ends and advantages mentioned, as well as others inherent therein. While a presently preferred embodiment of the disclosure has been given for purposes of disclosure, numerous changes exist in the details of procedures for accomplishing the desired results. These and other similar modifications will readily suggest themselves to those skilled in the art, and are intended to be encompassed within the spirit of the present disclosure disclosed herein and the scope of the appended claims.

What is claimed is:

1. A method of operating a traction device to detect blood flow patterns for intraneural facilitation (INF), the method comprising:
  providing the traction device to control traction, by one or more processors, so as to position a subject in one or more positions when positioned on one or more areas of the subject;
  receiving first signals, by the one or more processors, from a probe when the probe is positioned at a first area of the subject and when the traction device is positioned in a first position;
  processing the received first signals, via the one or more processors, to determine a first two-dimensional (2D) flow pattern measuring blood flow when being supplied from a first artery to a second artery supplying the blood flow to one or more nerves of the subject;
  moving the traction device to a second position, via the one or more processors, based at least in part on the determined first 2D flow pattern, thereby to control the blood flow for a first predetermined period of time;
  receiving second signals, by the one or more processors, from the probe when the probe is positioned at one or more second areas of the subject and when the traction device is positioned in the second position;
  processing the received second signals, via the one or more processors, to determine a second 2D flow pattern measuring the blood flow from the first artery to the second artery; and
  comparing the first 2D flow pattern and the second 2D flow pattern, via the one or more processors, to determine a first change in the blood flow through the second artery, thereby to provide vascular changes in the subject via INF.

2. The method according to claim 1, wherein the determined first change in the blood flow comprises a decrease in the blood flow through the second artery, the method further comprising:
  moving the traction device to a third position, via the one or more processors, based at least in part on the comparing, thereby to control the blood flow for a second predetermined period of time;
  receiving third signals, by the one or more processors, from the probe when the probe is positioned at the one or more second areas of the subject and when the traction device is positioned in the third position;
  processing the received third signals, via the one or more processors, to determine a third 2D flow pattern measuring the blood flow from the first artery to the second artery; and
  comparing the second 2D flow pattern and the third 2D flow pattern, via the one or more processors, to determine a second change in the blood flow through the second artery.

3. The method according to claim 2, wherein the determined second change in the blood flow comprises an increase in the blood flow through the second artery, the method further comprising:
  moving the traction device to a fourth position, via the one or more processors, based at least in part on the comparing, thereby to alter the blood flow;
  receiving fourth signals, by the one or more processors, from the probe when the probe is positioned at the one or more second areas of the subject and when the traction device is positioned in the fourth position;

processing the received fourth signals, via the one or more processors, to determine a fourth 2D flow pattern measuring the blood flow from the first artery to the second artery; and comparing the first 2D flow pattern and the fourth 2D flow pattern, via the one or more processors, to confirm the increase in blood flow through the second artery.

4. The method according to claim 1, wherein first area of the subject comprises an ulnar artery next to an ulnar nerve.

5. The method according to claim 1, wherein the first area of the subject comprises a foot joint.

6. The method according to claim 1, wherein the one or more second areas comprise one or more distal skin areas that are innervated by an ulnar nerve of the subject.

7. The method according to claim 1, wherein the processing of the first signals and the second signals comprises communicating the first signals and the second signals to an ultrasound machine, and wherein the ultrasound machine is configured to process aspects from the first signals and the second signals so as to calculate at least Volume Flow (VF) and Pulsatility Index (PI) for each of the first signals and the second signals.

8. The method according to claim 7, wherein the ultrasound machine is a Doppler ultrasound machine for converting Doppler measurements from the first area and from the one or more second areas into the first 2D flow pattern and into the second 2D flow pattern, the converting comprising:
(a) determining discriminant features of the Doppler measurements,
(b) plotting the discriminant features in two dimensions, and
(c) determining that the discriminant features cluster in areas of predetermined flow patterns representing a first flow condition or a second flow condition.

9. The method according to claim 8, wherein the discriminant features of the Doppler measurements include velocity values, and wherein:
the first flow condition is represented by first clusters including increasing velocity values above a time axis and a second cluster including receding velocity values below a time axis; and
the second flow condition is represented by third clusters including increasing velocity values above the time axis and two or more fourth clusters including receding velocity values below the time axis.

10. A system for operating a traction device to detect blood flow patterns for intraneural facilitation (INF), the system comprising:
one or more processors;
one or more traction devices to control traction, by the one or more processors, so as to position a subject in one or more positions when positioned on one or more areas of the subject;
one or more probes connected to the one or more processors to supply signals when applied to one or more areas of the subject; and
one or more memory devices in communication with the one or more processors and including instructions that, when executed by the one or more processors, cause the system to:
receive first signals from the probe when the probe is positioned at the first area of the subject and when the traction device is positioned in a first position;
process the received first signals to provide a first display of a first 2D flow pattern measuring blood flow when being supplied from a first artery to a second artery supplying the blood flow to one or more nerves of the subject;
move the traction device to a second position based at least in part on the determined first 2D flow pattern, thereby to control the blood flow for a first predetermined period of time;
receive second signals from the probe when the probe is positioned at one or more second areas of the subject and when the traction device is positioned in the second position thereby to control the blood flow for a first predetermined period of time;
process the received second signals to provide a second display of a second 2D flow pattern measuring the blood flow from the first artery to the second artery; and
compare the first 2D flow pattern and the second 2D flow pattern to determine a first change in the blood flow through the second artery, thereby to provide vascular changes in the subject via INF.

11. The system according to claim 10, wherein the determined first change in the blood flow comprises a decrease in the blood flow through the second artery, the instructions further configured to cause the system to:
move the traction device to a third position based at least in part on the comparing, thereby to control the blood flow for a second predetermined period of time;
receive third signals from the probe when the probe is positioned at the one or more second areas of the subject and when the traction device is positioned in a third position;
process the received third signals to provide a third display of a third 2D flow pattern measuring the blood flow from the first artery to the second artery; and
compare the second 2D flow pattern and the third 2D flow pattern to determine a second change in the blood flow through the second artery.

12. The system according to claim 11, wherein the determined second change in the blood flow comprises an increase in the blood flow through the second artery, the instructions further configured to cause the system to:
move the traction device to a fourth position based at least in part on the comparing, thereby to alter the blood flow;
receive fourth signals from the probe when the probe is positioned at the one or more second areas of the subject and when the traction device is positioned in the fourth position;
process the received fourth signals to provide a fourth display of a fourth 2D flow pattern measuring the blood flow from the first artery to the second artery; and
compare the first 2D flow pattern and the fourth 2D flow pattern to confirm the increase in blood flow through the second artery.

13. The system according to claim 10, wherein the first area of the subject comprises an ulnar artery next to an ulnar nerve.

14. The system according to claim 10, wherein the first area of the subject comprises a foot joint.

15. The system according to claim 10, wherein the at least one memory includes instructions that, when executed in the at least one processor, further cause the system to:
determine the one or more second areas in a distal skin area that is innervated by an ulnar nerve of the subject.

16. The system according to claim 10, the system further comprising an ultrasound machine configured to process the first signals and the second signals so as to calculate at least Volume Flow (VF) and Pulsatility Index (PI) for each of the first signals and the second signals.

17. The system according to claim 16, wherein the ultrasound machine is a Doppler ultrasound machine for converting Doppler measurements from the first area and from the one or more second areas into first 2D flow pattern and into the second 2D flow pattern, the converting by the instructions in the at least one memory that, when executed in the at least one processor, further cause the system to:
 (a) determine discriminant features of the Doppler measurements,
 (b) plot the discriminant features in two dimensions, and
 (c) determine that the discriminant features cluster in areas of predetermined flow patterns representing a first flow condition or a second flow condition.

18. The system according to claim 17, wherein the discriminant features of the Doppler measurements include velocity values, and wherein:

the first flow condition is represented by first clusters including increasing velocity values above a time axis and a second cluster including receding velocity values below a time axis; and the second flow condition is represented by third clusters including increasing velocity values above the time axis and two or more fourth clusters including receding velocity values below the time axis.

19. The system according to claim 16, the instructions further configured to cause the system to derive a ratio between a distal control value and a local circulation value based at least in part on the calculated VF and PI for each of the first signals and the second signals.

20. The system according to claim 19, the instructions further configured to cause the system to determine, based on the derived ratio, a percentage by which local neurovascular circulation is impacting one or more targeted nerves as compared to one or more nerves distal the first area at which the probe is positioned.

\* \* \* \* \*